United States Patent
Albrecht et al.

(10) Patent No.: US 12,185,932 B2
(45) Date of Patent: *Jan. 7, 2025

(54) WOUND RETRACTOR WITH MULTI-SEGMENT OUTER RING

(71) Applicant: Applied Medical Resources Corporation, Rancho Santa Margarita, CA (US)

(72) Inventors: Jeremy J. Albrecht, Rancho Santa Margarita, CA (US); Matthew M. Becerra, Lake Forest, CA (US); Eric Nguyen, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 18/182,927

(22) Filed: Mar. 13, 2023

(65) Prior Publication Data
US 2023/0210511 A1    Jul. 6, 2023

Related U.S. Application Data

(63) Continuation of application No. 16/739,796, filed on Jan. 10, 2020, now Pat. No. 11,602,338, which is a (Continued)

(51) Int. Cl.
*A61B 17/02* (2006.01)
*A61B 17/34* (2006.01)
*A61B 17/00* (2006.01)

(52) U.S. Cl.
CPC ...... *A61B 17/0293* (2013.01); *A61B 17/0218* (2013.01); *A61B 17/3431* (2013.01); (Continued)

(58) Field of Classification Search
CPC .................................. A61B 17/0293
See application file for complete search history.

(56) References Cited

U.S. PATENT DOCUMENTS

| | | |
|---|---|---|
| 52,014 A | 1/1866 | Bartlett |
| 202,813 A | 4/1878 | Hall |
| (Continued) | | |

FOREIGN PATENT DOCUMENTS

| | | |
|---|---|---|
| CN | 202751416 U | 2/2013 |
| DE | 26 05 148 A1 | 8/1977 |
| (Continued) | | |

OTHER PUBLICATIONS

European Patent Office, Extended European Search Report for European Patent Application No. 23175650.3, titled "Wound Retractor with Multi-Segment Outer Ring," dated Oct. 16, 2023, 8 pgs.
(Continued)

*Primary Examiner* — Andrew Yang
(74) *Attorney, Agent, or Firm* — Thomas Nguyen; Patrick Ikehara

(57) ABSTRACT

A retractor/protector suitable for use in a surgical incision or a natural orifice comprises a longitudinal axis defining an instrument access channel extending from a proximal end to a distal end; a flexible outer ring; an inner ring; a flexible sheath extending between the outer ring and the inner ring; and at least one rigid segment adapted to attach to the flexible outer ring to thereby increase the rigidity of the outer ring. Embodiments of the retractor/protector are described that have interlocking and non-interlocking rigid segments. Embodiments are also described that have bases that insert into or under the flexible outer ring in addition to or in lieu of rigid segments to increase rigidity and/or provide support for a detachable cap.

17 Claims, 36 Drawing Sheets

Related U.S. Application Data continuation of application No. 15/288,846, filed on Oct. 7, 2016, now Pat. No. 10,575,840.

(60) Provisional application No. 62/238,608, filed on Oct. 7, 2015.

(52) U.S. Cl.
CPC ............... *A61B 2017/00876* (2013.01); *A61B 2017/00902* (2013.01); *A61B 2017/0225* (2013.01); *A61B 2017/3435* (2013.01); *A61B 2017/3443* (2013.01); *A61B 2017/3492* (2013.01)

(56) References Cited

U.S. PATENT DOCUMENTS

| | | |
|---|---|---|
| 447,761 A | 3/1891 | Clough |
| 558,364 A | 4/1896 | Doolittle |
| 758,535 A | 4/1904 | Howden |
| 929,583 A | 7/1909 | Gibbs |
| 1,056,966 A | 3/1913 | Belding |
| 1,157,202 A | 10/1915 | Bates et al. |
| 1,221,123 A | 4/1917 | Westhaver |
| 1,242,972 A | 10/1917 | Petit |
| 1,598,284 A | 8/1926 | Kinney |
| 1,690,995 A | 11/1928 | Pratt |
| 1,810,466 A | 6/1931 | Deutsch |
| 2,219,564 A | 10/1940 | Reyniers |
| 2,305,289 A | 12/1942 | Coburg |
| 2,313,164 A | 3/1943 | Nelson |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,129,706 A | 4/1964 | Reynolds, Jr. |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,553,862 A | 1/1971 | Hamu |
| 3,570,475 A | 3/1971 | Weinstein |
| 3,656,485 A | 4/1972 | Robertson |
| 3,685,786 A | 8/1972 | Woodson |
| 3,703,896 A | 11/1972 | Nuwayser |
| 3,717,151 A | 2/1973 | Collett |
| 3,717,883 A | 2/1973 | Mosher |
| 3,729,006 A | 4/1973 | Wilder et al. |
| 3,729,027 A | 4/1973 | Bare |
| 3,729,045 A | 4/1973 | MacDonald |
| 3,762,080 A | 10/1973 | Poole |
| 3,774,596 A | 11/1973 | Cook |
| 3,782,370 A | 1/1974 | McDonald |
| 3,788,318 A | 1/1974 | Kim et al. |
| 3,789,852 A | 2/1974 | Kim et al. |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds, Jr. et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,863,639 A | 2/1975 | Kleaveland |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,082,005 A | 4/1978 | Erdley |
| 4,083,370 A | 4/1978 | Taylor |
| 4,096,853 A | 6/1978 | Weigand |
| 4,112,932 A | 9/1978 | Chiulli |
| 4,117,847 A | 10/1978 | Clayton |
| 4,130,113 A | 12/1978 | Graham |
| 4,141,364 A | 2/1979 | Schultze |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,189,880 A | 2/1980 | Ballin |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Benjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein et al. |
| 4,508,355 A | 4/1985 | Ditcher |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter et al. |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton, Jr. et al. |
| 4,691,942 A | 9/1987 | Ford |
| 4,714,749 A | 12/1987 | Hughes et al. |

(56) References Cited

U.S. PATENT DOCUMENTS

| | | |
|---|---|---|
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier et al. |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem et al. |
| 5,108,420 A | 4/1992 | Marks |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Rirchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,400 A | 9/1993 | Blake, III et al. |
| 5,242,409 A | 9/1993 | Buelna |
| 5,242,412 A | 9/1993 | Blake, III |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Sova et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke et al. |
| 5,300,035 A | 4/1994 | Clement |
| 5,300,036 A | 4/1994 | Mueller et al. |
| 5,303,486 A | 4/1994 | Dell |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,334,646 A | 8/1994 | Chen |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,473 A | 11/1994 | Winston et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Har et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,403,336 A | 4/1995 | Kieturakis et al. |
| 5,407,433 A | 4/1995 | Loomas |
| 5,411,483 A | 5/1995 | Loomas et al. |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Dubrul et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,454,365 A | 10/1995 | Bonutti |

(56) References Cited

U.S. PATENT DOCUMENTS

| | | | |
|---|---|---|---|
| 5,456,284 | A | 10/1995 | Ryan et al. |
| 5,460,170 | A | 10/1995 | Hammerslag |
| 5,460,616 | A | 10/1995 | Weinstein et al. |
| 5,468,248 | A | 11/1995 | Chin et al. |
| 5,476,475 | A | 12/1995 | Gadberry |
| 5,480,410 | A | 1/1996 | Cuschieri et al. |
| 5,486,426 | A | 1/1996 | McGee et al. |
| 5,490,843 | A | 2/1996 | Hildwein et al. |
| 5,492,304 | A | 2/1996 | Smith et al. |
| 5,496,280 | A | 3/1996 | Vandenbroek et al. |
| 5,503,112 | A | 4/1996 | Luhman et al. |
| 5,507,758 | A | 4/1996 | Thomason et al. |
| 5,508,334 | A | 4/1996 | Chen |
| 5,511,564 | A | 4/1996 | Wilk |
| 5,514,109 | A | 5/1996 | Mollenauer et al. |
| 5,514,133 | A | 5/1996 | Golub et al. |
| 5,514,153 | A | 5/1996 | Bonutti |
| 5,518,278 | A | 5/1996 | Sampson |
| 5,520,632 | A | 5/1996 | Leveen et al. |
| 5,522,791 | A | 6/1996 | Leyva |
| 5,522,824 | A | 6/1996 | Ashby |
| 5,524,644 | A | 6/1996 | Crook |
| 5,526,536 | A | 6/1996 | Cartmill |
| 5,531,758 | A | 7/1996 | Uschold et al. |
| 5,538,509 | A | 7/1996 | Dunlap et al. |
| 5,540,648 | A | 7/1996 | Yoon |
| 5,540,711 | A | 7/1996 | Kieturakis et al. |
| 5,545,150 | A | 8/1996 | Danks et al. |
| 5,545,179 | A | 8/1996 | Williamson, IV |
| 5,549,563 | A | 8/1996 | Kronner |
| 5,549,637 | A | 8/1996 | Crainich |
| 5,554,124 | A | 9/1996 | Alvarado |
| 5,555,653 | A | 9/1996 | Morgan |
| 5,562,632 | A | 10/1996 | Davila et al. |
| 5,562,677 | A | 10/1996 | Hildwein et al. |
| 5,562,688 | A | 10/1996 | Riza |
| 5,571,115 | A | 11/1996 | Nicholas |
| 5,571,137 | A | 11/1996 | Marlow et al. |
| 5,575,799 | A | 11/1996 | Bolanos et al. |
| 5,577,993 | A | 11/1996 | Zhu et al. |
| 5,578,048 | A | 11/1996 | Pasqualucci et al. |
| 5,580,344 | A | 12/1996 | Hasson |
| 5,584,850 | A | 12/1996 | Hart et al. |
| 5,601,579 | A | 2/1997 | Semertzides |
| 5,601,581 | A | 2/1997 | Fogarty et al. |
| 5,603,702 | A | 2/1997 | Smith et al. |
| 5,607,443 | A | 3/1997 | Kieturakis et al. |
| 5,620,415 | A | 4/1997 | Lucey et al. |
| 5,620,420 | A | 4/1997 | Kriesel |
| 5,628,732 | A | 5/1997 | Antoon, Jr. et al. |
| 5,632,284 | A | 5/1997 | Graether |
| 5,632,979 | A | 5/1997 | Goldberg et al. |
| 5,634,911 | A | 6/1997 | Hermann et al. |
| 5,634,936 | A | 6/1997 | Linden et al. |
| 5,634,937 | A | 6/1997 | Mollenauer et al. |
| 5,636,645 | A | 6/1997 | Ou |
| 5,640,977 | A | 6/1997 | Leahy et al. |
| 5,643,301 | A | 7/1997 | Mollenauer |
| 5,649,550 | A | 7/1997 | Crook |
| 5,651,771 | A | 7/1997 | Tangherlini et al. |
| 5,653,705 | A | 8/1997 | de la Torre et al. |
| 5,657,963 | A | 8/1997 | Hinchliffe et al. |
| 5,658,272 | A | 8/1997 | Hasson |
| 5,658,306 | A | 8/1997 | Kieturakis et al. |
| 5,662,615 | A | 9/1997 | Blake, III |
| 5,672,168 | A | 9/1997 | de la Torre et al. |
| 5,681,341 | A | 10/1997 | Lunsford et al. |
| 5,683,378 | A | 11/1997 | Christy |
| 5,685,854 | A | 11/1997 | Green et al. |
| 5,685,857 | A | 11/1997 | Negus et al. |
| 5,697,914 | A | 12/1997 | Brimhall |
| 5,707,703 | A | 1/1998 | Rothrum et al. |
| 5,709,664 | A | 1/1998 | Vandenbroek et al. |
| 5,713,858 | A | 2/1998 | Heruth et al. |
| 5,713,869 | A | 2/1998 | Morejon |
| 5,720,730 | A | 2/1998 | Blake, III |
| 5,725,536 | A | 3/1998 | Oberlin et al. |
| 5,728,103 | A | 3/1998 | Picha et al. |
| 5,730,748 | A | 3/1998 | Fogarty et al. |
| 5,735,791 | A | 4/1998 | Alexander, Jr. et al. |
| 5,738,628 | A | 4/1998 | Sierocuk et al. |
| 5,741,234 | A | 4/1998 | Aboul-Hosn |
| 5,741,298 | A | 4/1998 | MacLeod |
| 5,743,884 | A | 4/1998 | Hasson et al. |
| 5,749,882 | A | 5/1998 | Hart et al. |
| 5,753,150 | A | 5/1998 | Martin et al. |
| 5,755,660 | A | 5/1998 | Tyagi |
| 5,760,117 | A | 6/1998 | Chen |
| 5,769,783 | A | 6/1998 | Fowler |
| 5,782,812 | A | 7/1998 | Hart et al. |
| 5,782,817 | A | 7/1998 | Franzel et al. |
| 5,782,859 | A | 7/1998 | Nicholas et al. |
| 5,788,676 | A | 8/1998 | Yoon |
| 5,792,119 | A | 8/1998 | Marx |
| 5,794,528 | A | 8/1998 | Gronig et al. |
| 5,795,290 | A | 8/1998 | Bridges |
| 5,803,919 | A | 9/1998 | Hart et al. |
| 5,803,921 | A | 9/1998 | Bonadio |
| 5,803,923 | A | 9/1998 | Singh-Derewa et al. |
| 5,807,350 | A | 9/1998 | Diaz |
| 5,810,712 | A | 9/1998 | Dunn |
| 5,810,721 | A | 9/1998 | Mueller et al. |
| 5,813,409 | A | 9/1998 | Leahy et al. |
| 5,814,026 | A | 9/1998 | Yoon |
| 5,817,062 | A | 10/1998 | Flom et al. |
| 5,819,375 | A | 10/1998 | Kastner |
| 5,820,555 | A | 10/1998 | Watkins, III et al. |
| 5,820,600 | A | 10/1998 | Carlson et al. |
| 5,830,191 | A | 11/1998 | Hildwein et al. |
| 5,832,925 | A | 11/1998 | Rothrum |
| 5,836,871 | A | 11/1998 | Wallace et al. |
| 5,841,298 | A | 11/1998 | Huang |
| 5,842,971 | A | 12/1998 | Yoon |
| 5,848,992 | A | 12/1998 | Hart et al. |
| 5,853,395 | A | 12/1998 | Crook et al. |
| 5,853,417 | A | 12/1998 | Fogarty et al. |
| 5,857,461 | A | 1/1999 | Levitsky et al. |
| 5,860,995 | A | 1/1999 | Berkelaar |
| 5,865,728 | A | 2/1999 | Moll et al. |
| 5,865,729 | A | 2/1999 | Meehan et al. |
| 5,865,807 | A | 2/1999 | Blake, III |
| 5,865,817 | A | 2/1999 | Moenning et al. |
| 5,871,474 | A | 2/1999 | Hermann et al. |
| 5,876,413 | A | 3/1999 | Fogarty et al. |
| 5,879,368 | A | 3/1999 | Hoskin et al. |
| 5,882,344 | A | 3/1999 | Strouder, Jr. |
| 5,884,639 | A | 3/1999 | Chen |
| 5,894,843 | A | 4/1999 | Benetti et al. |
| 5,895,377 | A | 4/1999 | Smith et al. |
| 5,899,208 | A | 5/1999 | Bonadio |
| 5,899,913 | A | 5/1999 | Fogarty et al. |
| 5,904,703 | A | 5/1999 | Gilson |
| 5,906,577 | A | 5/1999 | Beane et al. |
| 5,913,847 | A | 6/1999 | Yoon |
| 5,916,198 | A | 6/1999 | Dillow |
| 5,916,232 | A | 6/1999 | Hart |
| 5,919,476 | A | 7/1999 | Fischer et al. |
| 5,931,832 | A | 8/1999 | Jensen |
| 5,947,922 | A | 9/1999 | MacLeod |
| 5,951,467 | A | 9/1999 | Picha et al. |
| 5,951,588 | A | 9/1999 | Moenning |
| 5,957,888 | A | 9/1999 | Hinchiffe |
| 5,957,913 | A | 9/1999 | de la Torre et al. |
| 5,961,539 | A | 10/1999 | Northrup, III et al. |
| 5,962,572 | A | 10/1999 | Chen |
| 5,964,781 | A | 10/1999 | Mollenauer et al. |
| 5,976,174 | A | 11/1999 | Ruiz |
| 5,989,232 | A | 11/1999 | Yoon |
| 5,989,233 | A | 11/1999 | Yoon |
| 5,989,266 | A | 11/1999 | Foster |
| 5,993,471 | A | 11/1999 | Riza et al. |
| 5,993,485 | A | 11/1999 | Beckers |
| 5,993,839 | A | 11/1999 | Mixon |
| 5,994,450 | A | 11/1999 | Pearce |

(56) References Cited

U.S. PATENT DOCUMENTS

| | | |
|---|---|---|
| 5,997,515 A | 12/1999 | de la Torre et al. |
| 6,004,303 A | 12/1999 | Peterson |
| 6,010,494 A | 1/2000 | Schäfer et al. |
| 6,017,355 A | 1/2000 | Hessel et al. |
| 6,018,094 A | 1/2000 | Fox |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,042,573 A | 3/2000 | Lucey |
| 6,045,535 A | 4/2000 | Ben Nun |
| 6,048,309 A | 4/2000 | Flom et al. |
| 6,050,871 A | 4/2000 | Chen |
| 6,053,934 A | 4/2000 | Andrews et al. |
| 6,059,816 A | 5/2000 | Moenning |
| 6,066,117 A | 5/2000 | Fox et al. |
| 6,068,639 A | 5/2000 | Fogarty et al. |
| 6,076,560 A | 6/2000 | Stähle et al. |
| 6,077,288 A | 6/2000 | Shimomura et al. |
| 6,086,603 A | 7/2000 | Termin et al. |
| 6,090,043 A | 7/2000 | Austin et al. |
| 6,099,506 A | 8/2000 | Macoviak et al. |
| 6,110,154 A | 8/2000 | Shimomura et al. |
| 6,123,689 A | 9/2000 | To et al. |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,154,991 A | 12/2000 | Duncan et al. |
| 6,159,182 A | 12/2000 | Davis et al. |
| 6,162,172 A | 12/2000 | Cosgrove et al. |
| 6,162,196 A | 12/2000 | Hart et al. |
| 6,162,206 A | 12/2000 | Bindokas et al. |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,197,002 B1 | 3/2001 | Peterson |
| 6,217,555 B1 | 4/2001 | Hart et al. |
| 6,217,590 B1 | 4/2001 | Levinson |
| 6,224,612 B1 | 5/2001 | Bates et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,533 B1 | 7/2001 | Fadem et al. |
| 6,254,534 B1 | 7/2001 | Butler et al. |
| 6,258,065 B1 | 7/2001 | Dennis et al. |
| 6,264,604 B1 | 7/2001 | Kieturakis et al. |
| 6,267,751 B1 | 7/2001 | Mangosong |
| 6,276,661 B1 | 8/2001 | Laird |
| 6,287,280 B1 | 9/2001 | Lampropoulos et al. |
| 6,315,770 B1 | 11/2001 | de la Torre et al. |
| 6,319,246 B1 | 11/2001 | de la Torre et al. |
| 6,322,541 B2 | 11/2001 | West et al. |
| 6,325,384 B1 | 12/2001 | Berry, Sr. et al. |
| 6,346,074 B1 | 2/2002 | Roth |
| 6,355,052 B1 | 3/2002 | Neuss et al. |
| 6,371,968 B1 | 4/2002 | Kogasaka et al. |
| 6,378,944 B1 | 4/2002 | Weisser |
| 6,382,211 B1 | 5/2002 | Crook |
| 6,383,162 B1 | 5/2002 | Sugarbaker |
| 6,391,043 B1 | 5/2002 | Moll et al. |
| 6,413,244 B1 | 7/2002 | Bestetti et al. |
| 6,413,458 B1 | 7/2002 | Pearce |
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,482,227 B1 | 11/2002 | Solovay |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,560,782 B2 | 5/2003 | Hourihan et al. |
| 6,569,120 B1 | 5/2003 | Green et al. |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,585,773 B1 | 7/2003 | Xie |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo, Jr. et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,901,870 B2 | 6/2005 | Eklöf et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,005 B2 | 8/2005 | Poff et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,958,069 B2 | 10/2005 | Shipp et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |

(56) References Cited

U.S. PATENT DOCUMENTS

| | | |
|---|---|---|
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,041,056 B2 | 5/2006 | Deslauriers et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Liu et al. |
| 7,105,009 B2 | 9/2006 | Johnson et al. |
| 7,105,607 B2 | 9/2006 | Chen |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racene et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,546 B2 | 3/2008 | Wulfman et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson et al. |
| 7,645,232 B2 | 1/2010 | Shluzas |
| 7,650,887 B2 | 1/2010 | Nguyen et al. |
| 7,661,164 B2 | 2/2010 | Chen |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,255 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,841,765 B2 | 11/2010 | Keller |
| 7,850,667 B2 | 12/2010 | Gresham |
| 7,867,164 B2 | 1/2011 | Butler et al. |
| 7,878,974 B2 | 2/2011 | Brustad et al. |
| 7,896,889 B2 | 3/2011 | Mazzocchi et al. |
| 7,909,760 B2 | 3/2011 | Albrecht et al. |
| 7,930,782 B2 | 4/2011 | Chen |
| 8,641,758 B1 | 2/2014 | Anderson et al. |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2002/0156432 A1 | 10/2002 | Racenet |
| 2002/0162559 A1 | 11/2002 | Crook |
| 2003/0004253 A1 | 1/2003 | Chen |
| 2003/0014076 A1 | 1/2003 | Mollenauer et al. |
| 2003/0028179 A1 | 2/2003 | Piskun |
| 2003/0040711 A1 | 2/2003 | Racenet et al. |
| 2003/0059865 A1 | 3/2003 | Nelson |
| 2003/0078476 A1 | 4/2003 | Hill |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0191371 A1 | 10/2003 | Smith et al. |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler et al. |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson et al. |
| 2004/0097793 A1 | 5/2004 | Butler et al. |
| 2004/0106942 A1 | 6/2004 | Taylor et al. |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 | 2/2005 | Ahlberg et al. |
| 2005/0033327 A1 | 2/2005 | Gainor et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0080319 A1 | 4/2005 | Dinkler et al. |
| 2005/0090713 A1 | 4/2005 | Gonzales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0159650 A1 | 7/2005 | Raymond et al. |
| 2005/0165281 A1 | 7/2005 | Ravikumar et al. |

(56) References Cited

U.S. PATENT DOCUMENTS

| | | |
|---|---|---|
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0215863 A1 | 9/2005 | Ravikumar et al. |
| 2005/0222582 A1 | 10/2005 | Wenchell |
| 2005/0228447 A1 | 10/2005 | Rambo |
| 2005/0240082 A1 | 10/2005 | Bonadio et al. |
| 2005/0241647 A1 | 11/2005 | Nguyen et al. |
| 2005/0251124 A1 | 11/2005 | Zvuloni et al. |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker et al. |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0088202 A1 | 4/2007 | Albrecht et al. |
| 2007/0088204 A1 | 4/2007 | Albrecht et al. |
| 2007/0093695 A1 | 4/2007 | Bonadio et al. |
| 2007/0118175 A1 | 5/2007 | Butler et al. |
| 2007/0142780 A1 | 6/2007 | Van Lue |
| 2007/0149859 A1 | 6/2007 | Albrecht et al. |
| 2007/0151566 A1 | 7/2007 | Kahle et al. |
| 2007/0156023 A1 | 7/2007 | Frasier et al. |
| 2007/0156024 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0270654 A1 | 11/2007 | Pignato |
| 2007/0270752 A1 | 11/2007 | LaBombard |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0103366 A1 | 5/2008 | Banchieri et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069627 A1 | 3/2009 | Haindl |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0182282 A1 | 7/2009 | Okihisa et al. |
| 2009/0187079 A1 | 7/2009 | Albrecht et al. |
| 2009/0227843 A1 | 9/2009 | Smith et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0063452 A1 | 3/2010 | Edelman et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0094227 A1 | 4/2010 | Albrecht et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegal et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1 | 10/2010 | Widenhouse et al. |
| 2010/0261975 A1 | 10/2010 | Huey et al. |
| 2010/0286484 A1 | 11/2010 | Stellon et al. |
| 2010/0298646 A1 | 11/2010 | Stellon et al. |
| 2010/0305407 A1 | 12/2010 | Farley |
| 2011/0021877 A1 | 1/2011 | Fortier et al. |
| 2011/0021879 A1 | 1/2011 | Hart et al. |
| 2011/0028891 A1 | 2/2011 | Okoniewski |
| 2011/0034935 A1 | 2/2011 | Kleyman |
| 2011/0034946 A1 | 2/2011 | Kleyman |
| 2011/0034947 A1 | 2/2011 | Kleyman |
| 2011/0054260 A1 | 3/2011 | Albrecht et al. |
| 2011/0071462 A1 | 3/2011 | Ewers et al. |
| 2011/0071463 A1 | 3/2011 | Ewers et al. |
| 2011/0144443 A1 | 6/2011 | Shelton, IV et al. |
| 2011/0160820 A1 | 6/2011 | Jackson et al. |
| 2012/0095297 A1 | 4/2012 | Dang et al. |
| 2013/0072759 A1 | 3/2013 | Li et al. |
| 2013/0245381 A1 | 9/2013 | Dang et al. |
| 2013/0296655 A1 | 11/2013 | Hart et al. |
| 2015/0018652 A1 | 1/2015 | Idowu et al. |
| 2015/0164552 A1 | 6/2015 | Chen et al. |

FOREIGN PATENT DOCUMENTS

| | | |
|---|---|---|
| DE | 33 36 279 C2 | 5/1985 |
| DE | 37 39 532 C1 | 12/1988 |
| DE | 37 37 121 A1 | 5/1989 |
| DE | 296 00 939 U1 | 6/1996 |
| DE | 19828009 A1 | 12/1999 |
| EP | 0 113 520 A2 | 7/1984 |
| EP | 0 142 262 A1 | 5/1985 |
| EP | 0 517 248 A1 | 12/1992 |
| EP | 0 537 768 A1 | 4/1993 |
| EP | 0 807 416 A2 | 11/1997 |
| EP | 0 849 517 B1 | 6/1998 |
| EP | 0 950 376 B1 | 10/1999 |
| EP | 1 118 657 A1 | 7/2001 |
| EP | 1 125 552 A1 | 8/2001 |
| EP | 1 312 318 B1 | 5/2003 |
| EP | 1 407 715 A1 | 4/2004 |
| EP | 1 609 429 A2 | 12/2005 |
| EP | 1 609 429 A3 | 12/2005 |
| EP | 2 044 889 A1 | 4/2009 |
| EP | 2 260 777 A1 | 12/2010 |
| EP | 2 272 450 A3 | 1/2011 |
| EP | 2 340 792 A1 | 7/2011 |
| EP | 2 486 882 A2 | 8/2012 |
| EP | 2 589 443 A1 | 5/2013 |
| EP | 2 609 880 A1 | 7/2013 |
| EP | 2 617 373 A1 | 7/2013 |
| FR | 1 456 623 | 7/1966 |

(56) References Cited

FOREIGN PATENT DOCUMENTS

| | | |
|---|---|---|
| GB | 1 151 993 A | 5/1969 |
| GB | 1 355 611 A | 6/1974 |
| GB | 1 372 491 A | 10/1974 |
| GB | 1 379 772 A | 1/1975 |
| GB | 1 400 808 A | 7/1975 |
| GB | 1 407 023 A | 9/1975 |
| GB | 1 482 857 A | 8/1977 |
| GB | 1 496 696 A | 12/1977 |
| GB | 2 071 502 A | 9/1981 |
| GB | 2 255 019 A | 10/1992 |
| GB | 2 275 420 A | 8/1994 |
| GB | 2 298 906 A | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S71634 | 2/1997 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 A | 4/1998 |
| JP | 11-290327 A | 10/1999 |
| JP | 2001-61850 A | 3/2001 |
| JP | 2002-28163 A | 1/2002 |
| JP | 2003-235879 A | 8/2003 |
| JP | 2004-195037 A | 7/2004 |
| JP | 2007-44395 A | 2/2007 |
| KR | 20140074622 A | 6/2014 |
| SU | 1342485 A1 | 10/1987 |
| WO | WO 86/06272 A1 | 11/1986 |
| WO | WO 86/06316 A1 | 11/1986 |
| WO | WO 92/11880 A1 | 7/1992 |
| WO | WO 92/21292 A2 | 12/1992 |
| WO | WO 93/05740 A1 | 4/1993 |
| WO | WO 93/14801 A1 | 8/1993 |
| WO | WO 94/04067 A1 | 3/1994 |
| WO | WO 94/22357 A2 | 10/1994 |
| WO | WO 95/05207 A2 | 2/1995 |
| WO | WO 95/07056 A2 | 3/1995 |
| WO | WO 95/22289 A2 | 8/1995 |
| WO | WO 95/24864 A1 | 9/1995 |
| WO | WO 95/27445 A1 | 10/1995 |
| WO | WO 95/27468 A1 | 10/1995 |
| WO | WO 96/36283 A1 | 11/1996 |
| WO | WO 97/11642 A1 | 4/1997 |
| WO | WO 97/32514 A2 | 9/1997 |
| WO | WO 97/32515 A1 | 9/1997 |
| WO | WO 97/42889 A1 | 11/1997 |
| WO | WO 98/19853 A1 | 5/1998 |
| WO | WO 98/35614 A1 | 8/1998 |
| WO | WO 98/48724 A1 | 11/1998 |
| WO | WO 99/03416 A1 | 1/1999 |
| WO | WO 99/15068 A2 | 4/1999 |
| WO | WO 99/16368 A1 | 4/1999 |
| WO | WO 99/22804 A1 | 5/1999 |
| WO | WO 99/25268 A1 | 5/1999 |
| WO | WO 99/29250 A1 | 6/1999 |
| WO | WO 00/32116 A1 | 6/2000 |
| WO | WO 00/32117 A1 | 6/2000 |
| WO | WO 00/32119 A1 | 6/2000 |
| WO | WO 00/32120 A1 | 6/2000 |
| WO | WO 00/35356 A1 | 6/2000 |
| WO | WO 00/47117 A1 | 8/2000 |
| WO | WO 00/54675 A1 | 9/2000 |
| WO | WO 00/54676 A1 | 9/2000 |
| WO | WO 00/54677 A1 | 9/2000 |
| WO | WO 01/08563 A2 | 2/2001 |
| WO | WO 01/08581 A2 | 2/2001 |
| WO | WO 01/26558 A1 | 4/2001 |
| WO | WO 01/26559 A1 | 4/2001 |
| WO | WO 01/045568 A1 | 6/2001 |
| WO | WO 01/49363 A1 | 7/2001 |
| WO | WO 01/91652 A1 | 12/2001 |
| WO | WO 02/07611 A2 | 1/2002 |
| WO | WO 02/17800 A2 | 3/2002 |
| WO | WO 02/34108 A2 | 5/2002 |
| WO | WO 03/011153 A1 | 2/2003 |
| WO | WO 03/011551 A1 | 2/2003 |
| WO | WO 03/026512 A1 | 4/2003 |
| WO | WO 03/032819 A1 | 4/2003 |
| WO | WO 03/034908 A2 | 5/2003 |
| WO | WO 03/034908 A3 | 5/2003 |
| WO | WO 03/061480 A1 | 7/2003 |
| WO | WO 03/077726 A2 | 9/2003 |
| WO | WO 03/103548 A1 | 12/2003 |
| WO | WO 2004/026153 A1 | 4/2004 |
| WO | WO 2004/030547 A1 | 4/2004 |
| WO | WO 2004/075730 A2 | 9/2004 |
| WO | WO 2004/075741 A2 | 9/2004 |
| WO | WO 2004/075930 A2 | 9/2004 |
| WO | WO 2005/009257 A2 | 2/2005 |
| WO | WO 2005/034766 A2 | 4/2005 |
| WO | WO 2005/089661 A1 | 9/2005 |
| WO | WO 2006/040748 A1 | 4/2006 |
| WO | WO 2006/057982 A2 | 6/2006 |
| WO | WO 2006/057982 A3 | 6/2006 |
| WO | WO 2006/059318 A1 | 6/2006 |
| WO | WO 2006/100658 A2 | 9/2006 |
| WO | WO 2007/044849 A1 | 4/2007 |
| WO | WO 2007/083305 A2 | 7/2007 |
| WO | WO 2007/083305 A3 | 7/2007 |
| WO | WO 2008/011358 A1 | 1/2008 |
| WO | WO 2008/015566 A2 | 2/2008 |
| WO | WO 2008/045935 A2 | 4/2008 |
| WO | WO 2008/093313 A1 | 8/2008 |
| WO | WO 2008/121294 A1 | 10/2008 |
| WO | WO 2009/117435 A2 | 9/2009 |
| WO | WO 2010/045253 A1 | 4/2010 |
| WO | WO 2010/082722 A1 | 7/2010 |
| WO | WO 2010/104259 A1 | 9/2010 |
| WO | WO 2010/141673 A1 | 12/2010 |
| WO | WO 2012/154845 A1 | 11/2012 |
| WO | WO 2013/106569 A2 | 7/2013 |
| WO | WO 2013/147461 A1 | 10/2013 |
| WO | WO 2014/174031 A1 | 10/2014 |

OTHER PUBLICATIONS

European Patent Office, Extended European Search Report for European Patent Application No. EP 22188302.8, titled "Wound Retractor," dated Oct. 12, 2022, 6 pgs.

European Patent Office, Extended European Search Report for European Patent Application No. EP 22189941.2, titled "Wound Retractor," dated Nov. 22, 2022, 6 pgs.

U.S. Appl. No. 10/381,220, filed Mar. 20, 2003; Title: Surgical Access Apparatus and Method, now U.S. Pat. No. 7,473,221 issued Jan. 6, 2009.

U.S. Appl. No. 10/436,522, filed May 13, 2003; Title: Laparoscopic Illumination Apparatus and Method, now U.S. Pat. No. 6,939,296 issued Sep. 6, 2005.

U.S. Appl. No. 10/399,209, filed Aug. 22, 2003; Title: Wound Retraction Apparatus and Method, now U.S. Pat. No. 6,958,037 issued Oct. 25, 2005.

U.S. Appl. No. 11/218,412, filed Sep. 1, 2005; Title: Wound Retraction Apparatus and Method, now U.S. Pat. No. 7,238,154 issued Jul. 3, 2007.

U.S. Appl. No. 10/399,057, filed Apr. 11, 2003; Title: Sealed Surgical Access Device, now U.S. Pat. No. 7,052,454 issued May 30, 2006.

U.S. Appl. No. 10/666,579, filed Sep. 17, 2003; Title: Surgical Instrument Access Device, now U.S. Pat. No. 7,163,510 issued Jan. 16, 2007.

(56) References Cited

OTHER PUBLICATIONS

U.S. Appl. No. 10/052,297, filed Jan. 18, 2002; Title: Hand Access Port Device, now U.S. Pat. No. 6,908,430 issued Jun. 21, 2005.
U.S. Appl. No. 08/015,765, filed Feb. 10, 1993; Title: Gas-Tight Sealaccomodating Surgical Instruments With a Wide Range of Diameters, now U.S. Pat. No. 5,407,433 issued Apr. 18, 1995.
U.S. Appl. No. 08/040,373, filed Mar. 30, 1993; Title: Gas-Tight Sealaccomodating Surgical Instruments With a Wide Range of Diameters, now U.S. Pat. No. 5,411,483 issued May 2, 1995.
U.S. Appl. No. 10/902,756, filed Jul. 29, 2004; Title: Hand Access Port Device, now abandoned.
U.S. Appl. No. 10/802,125, filed Mar. 15, 2004; Title: Surgical Guide Valve, now abandoned.
U.S. Appl. No. 10/516,198, filed Nov. 30, 2004; Title: Wound Retractor, now U.S. Pat. No. 7,650,887 issued Jan. 26, 2010.
U.S. Appl. No. 10/927,551, filed Aug. 25, 2004; Title: Surgical Access System, now abandoned.
U.S. Appl. No. 11/244,647, filed Oct. 5, 2005; Title: Surgical Access Apparatus and Method, now U.S. Pat. No. 7,481,765 issued Jan. 27, 2009.
U.S. Appl. No. 11/548,746, filed Oct. 12, 2006; Title: Method of Making a Hand Access Laparoscopic Device, now U.S. Pat. No. 7,749,415 issued Jul. 6, 2010.
U.S. Appl. No. 11/548,765, filed Oct. 12, 2006; Title: Split Hoop Wound Retractor, now U.S. Pat. No. 7,815,567 issued Oct. 26, 2010.
U.S. Appl. No. 11/548,767, filed Oct. 12, 2006; Title: Circular Surgical Retractor now U.S. Pat. No. 7,704,207 issued Apr. 27, 2010.
U.S. Appl. No. 11/548,781, filed Oct. 12, 2006; Title: Wound Retractor With Gel Cap, now U.S. Pat. No. 7,727,146 issued Jun. 1, 2010.
U.S. Appl. No. 11/548,955, filed Oct. 12, 2006; Title: Hand Access Laparoscopic Device, now U.S. Pat. No. 7,736,306 issued Jun. 15, 2010.
U.S. Appl. No. 11/755,305, filed May 30, 2007; Title: Wound Retraction Apparatus and Method, now U.S. Pat. No. 7,377,898 issued May 27, 2008.
U.S. Appl. No. 11/548,758, filed Oct. 12, 2006; Title: Split Hoop Wound Retractor With Gel Pad, now U.S. Pat. No. 7,909,760 issued Mar. 22, 2011.
U.S. Appl. No. 12/693,242, filed Jan. 1, 2010; Title: Wound Retractor, now U.S. Pat. No. 7,913,697 issued Mar. 29, 2011.
U.S. Appl. No. 12/768,328, filed Apr. 27, 2010; Title: Circular Surgical Retractor, now U.S. Pat. No. 7,892,172 issued Feb. 22, 2011.
U.S. Appl. No. 12/791,666, filed Jun. 1, 2010; Title: Wound Retractor With Gel Cap, now U.S. Pat. No. 7,883,461 issued Feb. 8, 2011.
U.S. Appl. No. 12/815,986, filed Jun. 15, 2010; Title: Hand Access Laparoscopic Device, now U.S. Pat. No. 7,878,974 issued Feb. 1, 2011.
U.S. Appl. No. 10/695,295, filed Oct. 28, 2003; Title: Surgical Gel Seal, now U.S. Pat. No. 8,262,622 issued Sep. 11, 2012.
U.S. Appl. No. 11/132,741, filed May 18, 2005; Title: Gas-Tight Sealaccomodating Surgical Instruments With a Wide Range of Diameters, now Re. 42,379 issued May 17, 2011.
U.S. Appl. No. 11/245,709, filed Oct. 7, 2005; Title: Surgical Access System, now U.S. Pat. No. 7,951,076 issued May 31, 2011.
U.S. Appl. No. 11/330,661, filed Jan. 12, 2006; Title: Sealed Surgical Access Device.
U.S. Appl. No. 11/564,409, filed Nov. 29, 2006; Title: Surgical Instrument Access Device, now U.S. Pat. No. 8,187,177 issued May 29, 2012.
U.S. Appl. No. 12/108,400, filed Apr. 23, 2008; Title: Wound Retraction Apparatus and Method, now U.S. Pat. No. 8,388,526 issued Mar. 5, 2013.
U.S. Appl. No. 12/119,371, filed May 12, 2008; Title: Surgical Retractor With Gel Pad, now U.S. Pat. No. 8,109,873 issued Feb. 7, 2012.
U.S. Appl. No. 12/119,414, filed May 12, 2008; Title: Surgical Retractor, now U.S. Pat. No. 8,226,552 issued Jul. 24, 2012.
U.S. Appl. No. 12/358,080, filed Jan. 22, 2009; Title: Surgical Instrument Access Device, now U.S. Pat. No. 8,343,047 issued Jan. 1, 2013.
U.S. Appl. No. 12/360,634, filed Jan. 27, 2009; Title: Surgical Access Apparatus and Method, now abandoned.
U.S. Appl. No. 12/360,710, filed Jan. 27, 2009; Title: Surgical Access Apparatus and Method, now U.S. Pat. No. 8,105,234 issued Jan. 31, 2012.
U.S. Appl. No. 12/578,422, filed Oct. 13, 2009; Title: Single Port Access System, now U.S. Pat. No. 8,262,568 issued Sep. 11, 2012.
U.S. Appl. No. 12/905,932, filed Oct. 15, 2010; Title: Split Hoop Wound Retractor, now U.S. Pat. No. 8,313,431 issued Nov. 20, 2012.
U.S. Appl. No. 12/960,449, filed Dec. 3, 2010; Title: Surgical Access Apparatus and Method, now U.S. Pat. No. 8,070,676 issued Dec. 6, 2011.
U.S. Appl. No. 12/960,458, filed Dec. 3, 2010; Title: Surgical Access Apparatus and Method, now U.S. Pat. No. 8,016,755 issued Sep. 13, 2011.
U.S. Appl. No. 13/006,727, filed Jan. 14, 2011; Title: Hand Access Laparoscopic Device, now U.S. Pat. No. 8,647,265 issued Feb. 11, 2014.
U.S. Appl. No. 13/008,728, filed Jan. 18, 2011; Title: Wound Retractor With Gel Cap, now U.S. Pat. No. 8,267,858 issued Sep. 18, 2012.
U.S. Appl. No. 13/023,334, filed Feb. 8, 2011; Title: Circular Surgical Retractor, now U.S. Pat. No. 8,414,487 issued Apr. 9, 2013.
U.S. Appl. No. 13/031,892, filed Feb. 22, 2011; Title: Wound Retractor, now U.S. Pat. No. 8,235,054 issued Aug. 7, 2012.
U.S. Appl. No. 13/050,042, filed Mar. 17, 2011; Title: Split Hoop Wound Retractor With Gel Pad, now U.S. Pat. No. 8,308,639 issued Nov. 13, 2012.
U.S. Appl. No. 10/446,365, filed May 28, 2003; Title: Screw-Type Seal With Inflatable Membrane, now Re. 44,790 issued Mar. 4, 2014.
U.S. Appl. No. 12/004,439, filed Dec. 20, 2007; Title: Skin Seal, now abandoned.
U.S. Appl. No. 12/004,441, filed Dec. 20, 2007; Title: Screw-Type Skin Seal With Inflatable Membrane, now abandoned.
U.S. Appl. No. 12/607,667, filed Oct. 28, 2009; Title: Screw-Type Skin Seal With Inflatable Membrane, now Re. 44,380 issued Jul. 16, 2003.
U.S. Appl. No. 10/965,217, filed Oct. 15, 2004; Title: Surgical Sealing Device, now abandoned.
U.S. Appl. No. 10/981,730, filed Nov. 5, 2004; Title: Surgical Sealing Device, now abandoned.
U.S. Appl. No. 11/246,909, filed Oct. 11, 2005; Title: Instrument Access Device, now U.S. Pat. No. 7,998,068 issued Aug. 16, 2011.
U.S. Appl. No. 11/291,089, filed Dec. 1, 2005; Title: A Surgical Sealing Device, now abandoned.
U.S. Appl. No. 11/486,383, filed Jul. 14, 2006; Title: Wound Retractor, now U.S. Pat. No. 8,021,296 issued Sep. 20, 2011.
U.S. Appl. No. 11/785,752, filed Apr. 19, 2007; Title: Instrument Access Device, now abandoned.
U.S. Appl. No. 12/244,024, filed Oct. 2, 2008; Title: Seal Anchor for Use in Surgical Procedures, now abandoned.
U.S. Appl. No. 12/578,832, filed Oct. 14, 2009; Title: Flexible Access Device for Use in Surgical Procedure, now abandoned.
U.S. Appl. No. 12/706,043, filed Feb. 16, 2010; Title: Flexible Port Seal, now U.S. Pat. No. 8,574,153 issued Nov. 5, 2013.
U.S. Appl. No. 12/719,341, filed Mar. 8, 2010; Title: Foam Port and Introducer Assembly, now U.S. Pat. No. 8,317,690 issued Nov. 27, 2012.
U.S. Appl. No. 10/895,546, filed Jul. 21, 2004; Title: Laparoscopic Instrumentand Cannula Assembly and Related Surgical Method, now U.S. Pat. No. 7,753,901 issued Jul. 13, 2010.
U.S. Appl. No. 10/913,565; filed Aug. 5, 2004; Title: Surgical Device With Tack-Free Gel and Method of Manufacture, now abandoned.

(56) References Cited

OTHER PUBLICATIONS

Declaration of John R. Brustad dated Dec. 10, 2009, submitted in U.S. Appl. No. 11/548,955, including Appendices A-D regarding product sales brochures and production drawings from 2001 and 2005, 7 pgs.
Dexterity Protractor Instruction Manual by Dexterity Surgical, Inc., 8 pgs.
European Patent Office, European Search Report for European Application No. EP 10 18 4681, entitled "Wound Retraction Apparatus and Method," dated Nov. 22, 2010, 4 pgs.
European Patent Office, European Search Report for European Application No. EP 10 18 4608, entitled "Wound Retraction Apparatus and Method," dated Nov. 22, 2010, 5 pgs.
European Patent Office, European Search Report for European Application No. EP 10 18 4648, entitled "Wound Retraction Apparatus and Method," dated Nov. 22, 2010, 4 pgs.
European Patent Office, European Search Report for European Application No. EP 10 18 4731, entitled "Wound Retraction Apparatus and Method," dated Nov. 22, 2010, 3 pgs.
European Patent Office, European Search Report for European Application No. EP 10 18 4661, entitled "Wound Retraction Apparatus and Method," dated Nov. 22, 2010, 4 pgs.
European Patent Office, European Search Report for European Application No. EP 10 18 4677, entitled "Wound Retraction Apparatus and Method," dated Nov. 22, 2010, 5 pgs.
European Patent Office, European Search Report for European Application No. EP 10 18 9325, entitled "Split Hoop Wound Retractor," dated Dec. 14, 2010, 3 pgs.
European Patent Office, European Search Report for European Application No. EP 10 18 9327, dated Dec. 14, 2010, entitled "Split Hoop Wound Retractor," 3 pgs.
European Patent Office, European Search Report for European Application No. EP 10 18 9328, entitled "Split Hoop Wound Retractor," dated Dec. 15, 2010, 3 pgs.
European Patent Office, European Search Report for European Application No. EP 04 00 2888, entitled "Hand Access Port Device," dated Sep. 10, 2004, 4 pgs.
European Patent Office, European Search Report for European Application No. EP 04 00 2889, entitled "Hand Access Port Device," dated Sep. 13, 2004, 4 pgs.
European Patent Office, International Search Report and The Written Opinion of theInternational Searching Authority for International Application No. PCT/US2006/040154, mailed Jan. 30, 2007, 9 pgs.
European Patent Office, International Search Report and The Written Opinion of theInternational Searching Authority for International Application No. PCT/US2006/040073, mailed Jan. 26, 2007, 8 pgs.
European Patent Office, International Search Report and The Written Opinion of the InternationalSearching Authority for International Application No. PCT/US2006/039905, mailed Jan. 17, 2007, 8 pgs.
European Patent Office, International Search Report and The Written Opinion of theInternational Searching Authority for International Application No. PCT/US2006/039883, mailed Jan. 31, 2007, 8 pgs.
European Patent Office, International Search Report and The Written Opinion of theInternational Searching Authority for International Application No. PCT/US2006/039800, mailed Apr. 16, 2007, 14 pgs.
European Patent Office, International Search Report and The Written Opinion of theInternational Searching Authority for International Application No. PCT/US2006/039799, mailed Mar. 27, 2007, 11 pgs.
European Patent Office, European Search Report for European Patent No. 11172709.5, dated Aug. 16, 2011, 4 pgs.
European Patent Office, European Search Report for European Patent No. 11172706.1, dated Aug. 16, 2011, 3 pgs.
European Patent Office, European Search Report for European Application No. 15173370.6, dated Aug. 7, 2015, entitled "Wound Retractor," 3 pgs.
European Search Report for corresponding EP 08253236, mailed Feb. 10, 2009, 6 pgs.
European Patent Office, European Search Report for European Patent No. 12151288, dated Feb. 10, 2012, 8 pgs.
European Patent Office, Supplementary European Search Report for European U.S. Appl. No. 08/755,322, dated Apr. 18, 2012, 3 pgs.
European Patent Office, Supplementary European Search Report for European U.S. Appl. No. 08/755,336, dated Jun. 15, 2012, 2 pgs.
Harold W. Harrower, M.D. Isolation of Incisions into Body Cavities, The American Journal of Surgery, p. 824-826.
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinionof the International Searching Authority for International Application No. PCT/US04/05484, mailed Nov. 12, 2004, 9 pgs.
International Searching Authority/US, International Search Report and the Written Opinionof the International Searching Authority for International Application No. PCT/US01/29682, mailed Jun. 14, 2002, 8 pgs.
Kagaya, Laparascopic cholecystecomy via two ports, using the "Twin-Port" system, J. Hepatobiliary Pancreat Surg (2001) 8:76-80.
McSweeney, Cannulation of the Rumen in Cattle and Buffaloes, Australian Veterinary Journal, Aug. 1989, vol. 66, No. 8, pp. 266-268.
Neil Sheehan, Supplemental Expert Report of Neil Sheehan, Re: U.S. Pat. No. 5,741,298, United States District Court for the Central District of California, Civil Action No. SACV 03-1322 JVS, Aug. 9, 2005, 16 pgs.
Office Action in co-pending U.S. Appl. No. 12/360,634, dated Jan. 24, 2011 in 12 pages.
Office Action in co-pending U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan, 5 pgs.
The International Bureau of WIPO, International Preliminary Report on Patentability, dated Aug. 29, 2006, for International Application No. PCT/US2004/028250, 8 pgs.
The International Bureau of WIPO, International Preliminary Report on Patentability, dated Apr. 16, 2008, for International Application No. PCT/US2006/039799, 7 pgs.
The International Bureau of WIPO, International Preliminary Report on Patentability for International Application No. PCT/US2006/039800, dated Apr. 16, 2008, 9 pgs.
Yamazaki, et al., Diurnal Changes in the Composition of Abomasal Digesta in Fasted and FedSheep, The Tohoki Journal of Agricultural Research, Mar. 1987, vol. 37, No. 3-4, pp. 49-58.
International Search Report and Written Opinion in PCT/IE2005/000113, mailed on Feb. 22, 2006, 8 pgs.
International Search Report and Written Opinion in PCT/IE2007/000050, mailed on Aug. 13, 2007, 7 pgs.
The International Searching Authority, The International Search Report and Written Opinion of the International Searching Authority for International Application No. PCT/US08/63445, mailed Sep. 29, 2008, 11 pgs.
The International Searching Authority, The International Search Report and Written Opinion of the International Searching Authority for International Application No. PCT/US08/063463, mailed Sep. 10, 2008, 9 pgs.
The International Bureau of WIPO, International Preliminary Report on Patentability for International Application No. PCT/US2008/063463, entitled "Surgical Retractor," dated Nov. 17, 2009, 5 pgs.

(56) References Cited

OTHER PUBLICATIONS

The International Bureau of WIPO, International Preliminary Report on Patentability for International Application No. PCT/US08/63445, entitled "Surgical Retractor with Gel Pad," issued Nov. 17, 2009, 5 pgs.

International Searching Authority—US, International Search Report and Written Opinion of the International Searching Authority for International Application No. PCT/US04/25511, mailed Nov. 7, 2007, 12 pgs.

The International Bureau of WIPO, International Report on Patentability for International Application No. PCT/US04/25511, mailed Dec. 6, 2007, 6 pgs.

The International Bureau of WIPO, International Preliminary Report on Patentability, for International Application No. PCT/US2012/037111, titled "Wound Retractor," dated Nov. 12, 2013, 15 pgs.

International Search Report and Written Opinion of the International Searching Authority for PCT application No. PCT/US01/29682, 8 pgs.

European Patent Office, The International Search Report and Written Opinion for International Application No. PCT/US2015/045058, titled "Wound Retractor," mailed Nov. 12, 2015, 16 pgs.

The International Searching Authority, The International Search Report and WrittenOpinion of the International Searching Authority for International Application No. PCT/US2015/062326, mailed Jun. 21, 2016, 22 pgs.

European Patent Office, European Search Report for European Patent No. 16167739.8, dated Aug. 10, 2016, 4 pgs.

The International Bureau of WIPO, International Preliminary Report on Patentability for International Application No. PCT/US2015/045058, dated Feb. 23, 2017, 12 pgs.

European Patent Office, The International Search Report and Written Opinion for International Application No. PCT/US2011/054266, titled "Natural Orifice Surgery System," mailed Feb. 9, 2012, 13 pages.

European Patent Office, The International Search Report and Written Opinion for International Application No. PCT/US2012/037111, "Wound Retractor," mailed Aug. 30, 2012, 21 pgs.

The International Bureau of WIPO, International Preliminary Report on Patentability for International Application No. PCT/US2011/054266, titled "Natural Orifice Surgery System", dated Apr. 2, 2013, 8 pgs.

European Patent Office, The International Written Opinion for International Application No. PCT/US2013/037213, titled "Natural Orifice Surgery System," mailed Jul. 3, 2013, 6 pgs.

The International Bureau of WIPO, International Preliminary Report on Patentability for International Application No. PCT/US2013/037213, titled "Natural Orifice Surgery System," dated Oct. 21, 2014, 8 pgs.

European Patent Office, The International Search Report and Written Opinion for International Application No. PCT/US2012/060997, titled "Simulated Tissue Structure for Surgical Training," mailed Mar. 7, 2013 8 pgs.

European Patent Office, The International Search Report and Written Opinion for International Application No. PCT/US2015/045201, titled "Natural Orifice Surgery System," mailed Sep. 25, 2015, 11 pgs.

European Patent Office, The International Search Report for International Application No. PCT/US2013/0037213, titled "Natural Orifice Surgery System," mailed Jul. 3, 2013, 3 pgs.

The International Bureau of WIPO, International Preliminary Report on Patentability for International Application No. PCT/US2015/045201, titled "Natural Orifice Surgery System", dated Mar. 2, 2017, 9 pgs.

European Patent Office, The International Search Report and Written Opinion of the International Searching Authority for International Application No. PCT/US2016/049079, titled "Wound Retractors with Non-Circular, Non-Coplanar or Non-Parallel Inner Rings," mailed Apr. 5, 2017, 21 pgs.

The International Bureau of WIPO, International Preliminary Report on Patentability for International Application No. PCT/US2015/062326, titled "Circumferential Wound Retraction with Support and Guidance Structures," dated Jun. 8, 2017, 16 pgs.

European Patent Office, The International Search Report and Written Opinion of the International Searching Authority for International Application No. PCT/US2016/056109, titled "Wound Retractor with Multi-Segment Outer Ring," mailed Jul. 10, 2017, 36 pgs.

The International Bureau of WIPO, International Preliminary Report on Patentability for International Application No. PCT/US2016/049079, titled "Wound Retractors with Non-Circular, Non-Coplanar or Non-Parallel Inner Rings," dated Mar. 8, 2018, 12 pgs.

The International Bureau of WIPO, International Preliminary Report on Patentability for International Application No. PCT/US2016/056109, titled "Wound Retractor with Multi-Segment Outer Ring," dated Apr. 19, 2018, 11 pgs.

European Patent Office, European Search Report for European Application No. EP 10207981.4, entitled "Wound Retractor," dated Jan. 2, 2019, 13 pgs.

European Patent Office, Extended European Search Report for European Patent Application No. EP 19152405.7, titled "Natural Orifice Surgery System," dated May 6, 2019, 7 pgs.

European Patent Office, Extended European Search Report for European Patent Application No. EP 20169466.8, titled "Wound Retractor," dated Jul. 24, 2020, 7 pgs.

WOUND RETRACTOR WITH MULTI-SEGMENT OUTER RING

CROSS REFERENCE TO RELATED APPLICATIONS

This application is a continuation of U.S. patent application Ser. No. 16/739,796, filed Jan. 10, 2020, which is a continuation of U.S. patent application Ser. No. 15/288,846, filed Oct. 7, 2016, now issued as U.S. Pat. No. 10,575,840, which claims the benefit of U.S. Application No. 62/238,608, filed Oct. 7, 2015, the entire disclosure of which is incorporated by reference.

TECHNICAL FIELD

This invention generally relates to medical devices and, more specifically, to a wound retractors having detachable rigid segments attached to the outer rings of the retractor or protector.

DISCUSSION OF THE RELEVANT ART

Wound retractors/protectors have been described in U.S. Pat. Nos. 7,650,887; 7,727,146; 7,883,461; 7,913,697; 8,235,054, and 8,267,858, the disclosures of which are hereby incorporated by reference in their entireties. The basic components of such wound retractors include an outer ring or rings, an inner ring, and a flexible sheath or sleeve attached at either end to the outer and inner ring.

The outer ring or rings of the wound retractor may be flexible or rigid. In general, flexible outer rings are more comfortable and easier to deploy, while rigid outer rings provide better retraction and, optionally, serve as a platform for attachment of a cap or other similar devices. What is needed, therefore, is a retractor having an outer ring that combines the comfort and ease of deployment of a flexible ring with the retraction and functionality of a rigid ring.

SUMMARY

A retractor/protector suitable for use in a surgical incision or a natural orifice comprises a flexible outer ring, an inner ring, a flexible sheath extending between the outer ring and the inner ring, a longitudinal axis defining an instrument access channel extending through the flexible sheath from the flexible outer ring at a proximal end to the inner ring at a distal end and a rigid segment adapted to detachably connect to the flexible outer ring to thereby increase the rigidity of the outer ring. In some embodiments there are two rigid segments, while in other embodiments there are more than two rigid segments detachably connected to the outer ring. In some embodiments, the rigid segments are interlockable. In some interlockable examples, the rigid segments may have a boss on one end and a recess on the other end, the recess configured to receive the boss of a contiguous rigid segment.

In another embodiment of the present invention, the rigid attachment is in the form of a ring-shaped rigid base. The ring-shaped rigid base may have an annular groove circumscribed around the outer circumference of the base, the groove configured to receive the outer ring. In this embodiment, the outer ring can be snap fit into the rigid base to provide rigidity when needed.

In still another embodiment of the present invention, the outer ring is detachable from the flexible sheath. In this embodiment, the outer ring comprises a first magnetic strip. The flexible sheath has a second magnetic strip disposed at the proximal end of the sheath, such that the outer ring is detachably connected to the proximal end of the flexible sheath by magnetic attraction between the first magnetic strip and the second magnetic strip. In alternative embodiments, the outer ring comprises a first tube and a second tube, wherein a rigid support ring is disposed within the first lumen and the first magnetic strip is disposed within the second lumen. In some embodiments, a cap may be detachably connected to the outer ring.

DETAILED DESCRIPTION

Wound retractors/protectors have been described in U.S. Pat. Nos. 7,650,887; 7,727,146; 7,883,461; 7,913,697; 8,235,054, and 8,267,858, and U.S. application Ser. No. 12/873,115, the disclosures of which are hereby incorporated by reference in their entireties.

Figure 1:
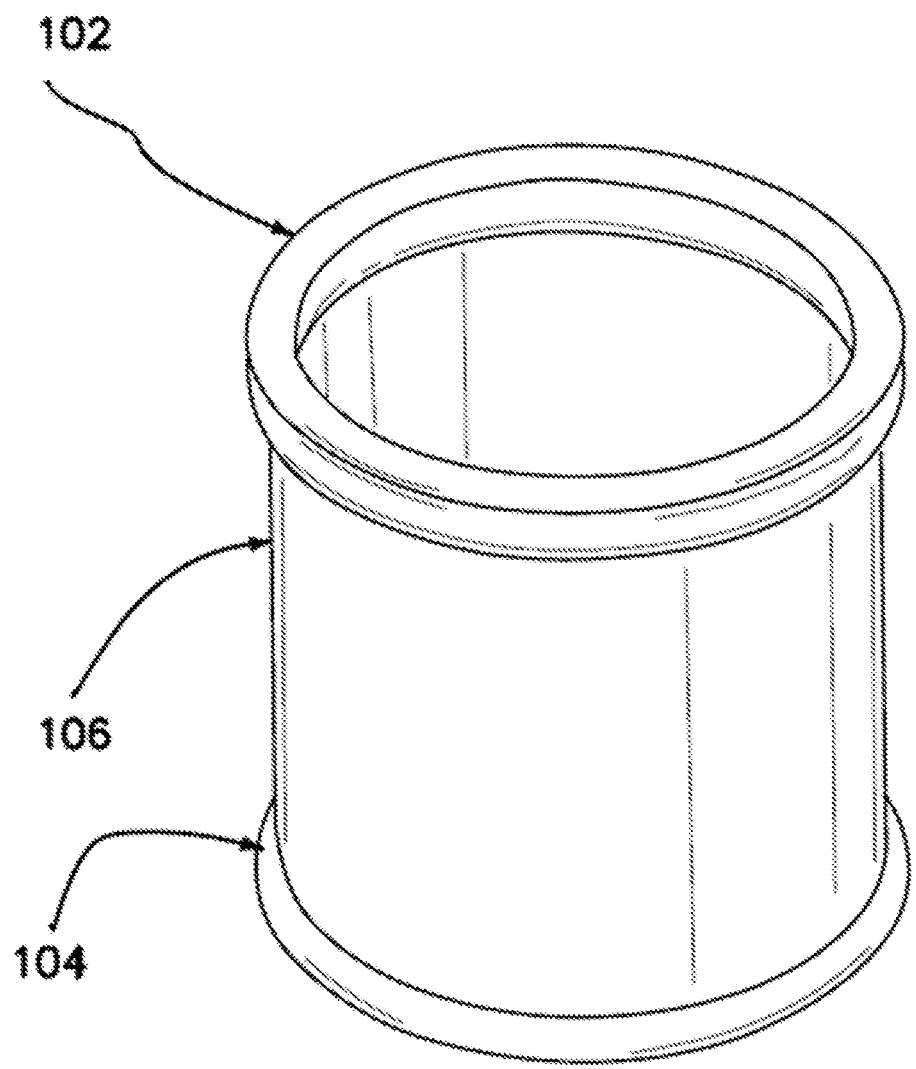
FIG. 1 illustrates an isometric view of an adjustable wound retractor.

FIG. 1 illustrates an adjustable wound retractor 100 useful in a variety of surgical procedures. The wound retractor 100 includes an outer ring 102, an inner ring 104, and a distensible sheath 106 coupling the outer ring and the inner ring. Outer ring 102 is shown as a single ring, but may also be a double ring or triple ring or multiples thereof. In the illustrated embodiment, the outer ring 102 comprises an annular axis around which the outer ring 102 is rotatable or invertible in a process through which the outer ring 102 is rolled through itself.

To facilitate rolling and to provide for enhanced comfort, the outer ring 102 preferably comprises a flexible material. In some embodiments, the flexible material comprises one or more polymers, for example, flexible engineering plastics. In some embodiments, the flexible material comprises an elastomer, for example, a thermoplastic elastomer. In some embodiments, the outer ring 102 comprises a composite, for example, a polymer and a reinforcing material. Examples of suitable reinforcing materials include fibers, fabrics, and the like, which comprise at least one of polymer, metal, glass, ceramic, and the like. Embodiments of the outer ring 102 are molded and/or extruded as a single piece or as a plurality of pieces that are assembled into the outer ring 102.

Figure 8A:
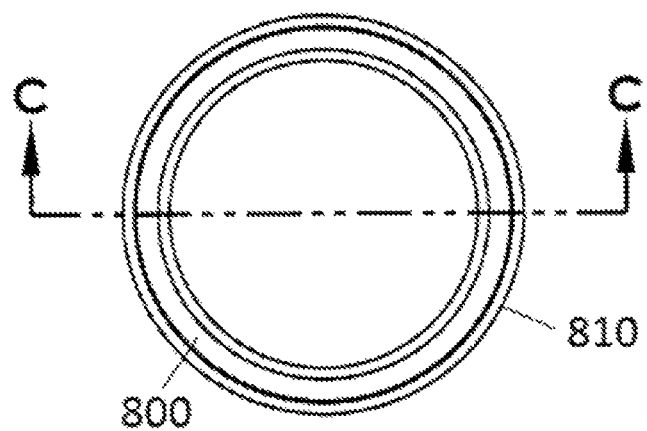
FIG. 8A illustrates the outer ring and rigid base of FIGS. 7A-C, shown in top view.
Figure 8B:
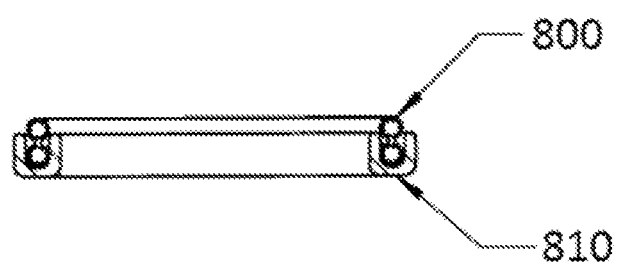
FIG. 8B illustrates the outer ring and rigid base of FIGS. 7A-C, shown in cross-sectional view.
Figure 8C:
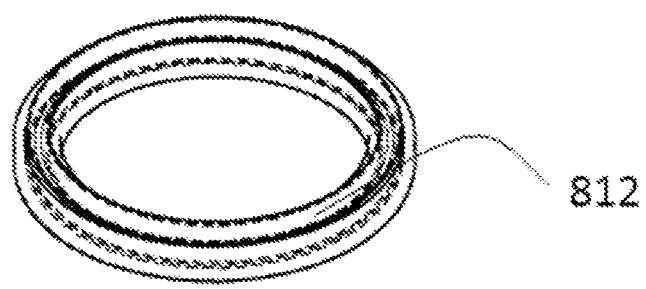
FIG. 8C illustrates the outer ring and rigid base of FIGS. 7A-C, shown in perspective view.

In the illustrated embodiment, a cross-sectional shape of the outer ring 102 is generally a figure-8, or first circle and a second circle joined by a web extending therebetween. The outer ring may be solid or may have one or more lumens disposed in the ring. Other embodiments of the outer ring have different cross-sectional shapes, for example, generally oval or elliptical; diamond-shaped or rhomboid; hourglass or dog bone shaped; snowman-shaped; radially flat (washer-shaped outer ring), longitudinally flat (cylindrical outer ring), or flat at another angle (frustoconical outer ring); circular (toroidal outer ring), X-shaped, triangular, square, hexagonal, polygonal, and the like. Some embodiments of the outer ring comprise one or more gripping surfaces that facilitate manually rolling the outer ring around the annular axis thereof. Examples of suitable gripping surfaces include generally flattened surfaces and concave surfaces. Some embodiments of the outer ring 102 have a Möbius configuration in which the outer ring 102 is fabricated with a preloaded circumferential torsional stress, for example, by twisting an elongate member followed by joining the ends.

In some hollow embodiments of the outer ring 102, a wire or rod is disposed in at least one first lumen. Some embodiments of the outer ring 102 do not comprise a rod or wire disposed in a lumen thereof. Some embodiments of a non-compliant outer ring 102 facilitate direct coupling of another device to the outer ring 102 for example, a lid, cap, and/or gel cap. Some embodiments of a compliant outer ring 102 conform to a body surface.

Returning to FIG. 1, the sheath 106 may be coupled to the outer ring 102 and the inner ring 104 by heat seal, adhesive, or other means that are well known in the art. The sheath 106 may be made of a material that is flexible and impermeable to fluids and bacteria.

Embodiments of the sheath comprise sheets, membranes, fibers, and/or strands of one or more materials that endow the sheath with the abrasion and puncture resistance. Suitable sheets, membranes, fibers, and/or strands comprise at least one of natural polymers, semi-synthetic polymers, synthetic polymers, metal, ceramic, glass, carbon fiber, carbon nanotubes, and the like. Suitable natural polymers include cellulose, silk, and the like. Semi-synthetic fibers include nitrocellulose, cellulose acetate, rayon, and the like. Suitable synthetic fibers include polyester, aromatic polyester, polyamide (NYLON®, DACRON®), aramid (KEVLAR®), polyimide, polyolefin, polyethylene (SPECTRA®), polyurethane, polyurea, polyvinyl chloride (PVC), polyvinylidene chloride, polyether amide (PEBAX®), polyether urethane (PELLETHANE®), polyacrylate, polyacrylonitrile, acrylic, polyphenylene sulfide (PPS), polylactic acid (PLA), poly(diimidazopyridinylene-dihydroxyphenylene) (M-5); poly(p-phenylene-2,6-benzobisoxazole) (ZYLON®), liquid crystal polymer fiber (VECTRAN®), and the like, and blends, copolymers, composites, and mixtures thereof. Suitable metals include stainless steel, spring steel, nitinol, super elastic materials, amorphous metal alloys, and the like.

Some embodiments of the sheath material comprises a composite comprising a fabric or textile, for example, at least one of a coated fabric, a laminated fabric, and a fabric embedded in a polymer. Coatings and/or laminations are disposed on one face or both faces of the fabric. Suitable coatings and laminating materials include polymers, for example, at least one of polyurethane, polyether, PVC, polyvinylidene chloride, silicone, styrene-butadiene, polyethylene, polypropylene, ethylene-propylene copolymer, polyisoprene, ethylene vinyl acetate (EVA), ethylene-propylene-diene monomer (EPDM), polyamide (MYLAR®), polyether block amide (PEBAX®), polyether urethane (PELLETHANE®), composites, blends, mixtures, and the like. An example of a suitable composite fabric is polyurethane laminated fabric (PUL). Some embodiments of the coating or lamination modify gas and/or moisture permeability through the sheath material, for example, by controlling the size of pores therethrough. For example, decreasing moisture permeability reduces dehydration of the retracted tissue and/or creates a barrier to pathogens such as bacteria. Increasing gas and moisture permeability permits hydrating and/or oxygenating the retracted tissue. Some materials are selectively permeable to certain fluids. For example, some embodiments of PVC are oxygen permeable and moisture impermeable, thereby permitting simultaneously oxygenating tissue while reducing dehydration. Some embodiments of the coating or lamination comprise an antibacterial or antimicrobial agent. In some embodiments, the antibacterial or antimicrobial agent is a surface agent or is integral to the material. Examples of suitable antibacterial or antimicrobial agents include iodine, antibiotics, silver, triclosan, biocides, and the like. Some embodiments of the coating or lamination provide a smoother and/or lower friction inside surface, which reduces the likelihood of instrument damage to the sheath.

Some embodiments of the sheath comprise a composite comprising a fiber-reinforced polymer film or membrane. Suitable fibers or strands are discussed above. Suitable polymer film materials include at least one of materials discussed above as coating and laminating materials. In some embodiments, the fibers are sandwiched between polymer film layers. In some embodiments, the polymer film layers are independently selected. For example, in some embodiments, the outer layer provides desirable tissue contact properties discussed above, while the inner layer is puncture resistant.

Some embodiments of the sheath comprise a plurality of layers, for example, a fabric layer and a polymer film layer, or a fabric layer sandwiched between polymer film layers. In some embodiments, the layers are secured to each other. In other embodiments, the layers are independent of, or not secured to each other, for example, a polymer film layer and a layer comprising a plurality of strips or bands as discussed above.

Some embodiments of the sheath comprise a fluid-permeable layer disposed on a fluid-impermeable layer, with the fluid-impermeable layer disposed on the inside of the sheath. The fluid-permeable layer contacts the wound margins, thereby permitting a user to supply pressurized fluid and/or apply vacuum to the wound margins. For example, in some embodiments, oxygen, moisture, therapeutic agent, and/or other fluids are supplied to the wound margins. In some embodiments, applying vacuum promotes bleeding, thereby reducing tissue necrosis. Embodiments of the fluid-permeable layer comprise at least one of open cell foam, fabrics, non-woven fabrics, and knit fabrics.

In some embodiments, at least a portion of the sheath is transparent, thereby providing a view of the retracted tissue. In some embodiments comprising a polymer membrane or film, the polymer membrane or film is transparent.

The inner ring 104 may be made of materials of sufficient hardness to retain its shape after insertion into a body cavity 904 (FIG. 2) but sufficiently flexible so as to allow the inner ring to be compressed for insertion through an incision. The materials of which the outer ring 102 is made must allow the outer ring to be turned around its annular axis as further described below. The shape of the outer ring 102 affects both its ability to grip and to provide stability during and after adjustment.

Figure 2:
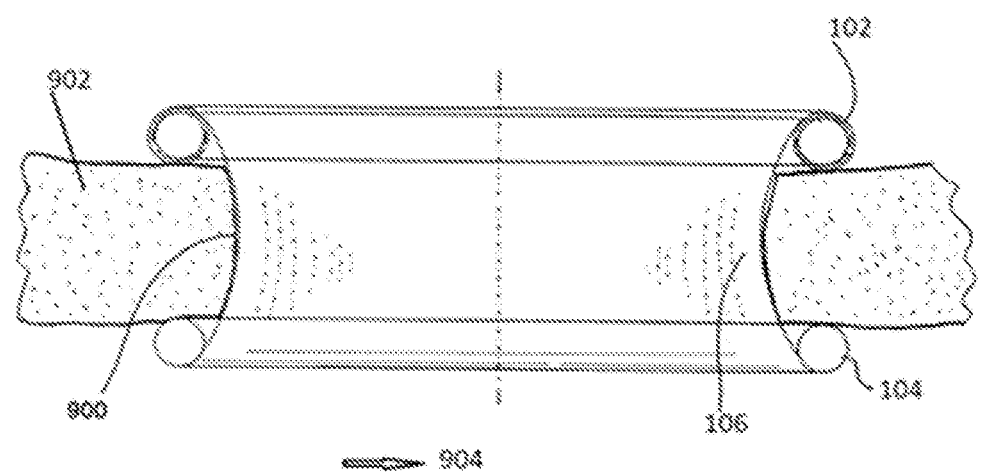
FIG. 2 is a cross-sectional view of a wound retractor deployed in an incision.

FIG. 2 illustrates the wound retractor deployed in a wound opening 900. To deploy the wound retractor, an incision in the shape of a slit is first made in the body wall 902 of a patient, such as the abdominal wall 902. The inner ring 104 is compressed and the inner ring and sheath 106 are manually inserted into the body cavity 904 through the incision with the outer ring 102 remaining external to the body cavity. Once the inner ring 104 is within the body cavity 904, it expands around the inner surface of the incision 900 so as to be generally parallel to the outer surface of the abdominal wall 902. The sheath 106 provides a working channel from outside the body cavity 904 to inside the body cavity.

The outer ring 102 initially rests above the abdominal wall 902 around the wound opening 900. Since the upper end of the sheath 106 is coupled to the outer ring 102, the sheath 106 can be drawn upwards and radially outward or inward, thereby drawing the inner ring 104 tightly against the inner surface of the abdominal wall 902. Moreover, the intermediate portion of the sheath 106 is drawn tightly against the sides and edges of the wound opening 900, thereby retracting the adjacent tissue and producing a tightly sealed opening in the body cavity 904. The sheath 106 contacts the entire surface of the wound 900 and protectively covers and seals it from contamination and infection. Depending on the size and depth of the incision 900, the user can roll up the sheath 106 by gripping the outer ring 102 and rotating it until the sheath 106 abuts the outer edge of the wound opening 900. The inner ring 104 is adapted for juxtaposition with the inner surface of the abdominal wall 902 and the outer ring 102 is adapted for juxtaposition with the outer surface of the abdominal wall. Both the inner ring 104 and the outer ring 102 are adapted for disposition relative to the incision 900 in the abdominal wall 902. The sheath 106 is adapted to traverse the incision 900 in the abdominal wall 902.

After surgery, the wound retractor 100 may be retrieved by grabbing the inner ring 104 and the sheath 106 and pulling them through the wound opening 900. The use of the sheath 106 and the ease of retracting the outer ring 102 provide higher compression between the inner and outer rings. As a result, the wound retractor 100 provides incremental adjustability to fit a wide range of incision sizes and isolates and protects the wound from bacterial infection as diseased body parts and contaminated instruments are passed through the wound.

FIGS. 3 and 4 illustrate a new wound retractor, in which the outer ring system is designed to provide the user with both flexibility for ease of deployment and rigidity for full retraction once deployed. The outer ring system comprises a flexible outer ring 800 and one or more interchangeable rigid segments 802 that can be attached to the flexible ring to provide rigidity to the outer ring while in the resting state. The rigid segments can be strategically placed along the retracted wound where, for example, constant maximum visualization is required.

In some embodiments, the rigid segments are designed to snap fit onto the flexible outer ring, and may be partially or continuously placed along the circumference of the flexible ring based on the user's preference and desired degree of rigidity.

Figure 3A:
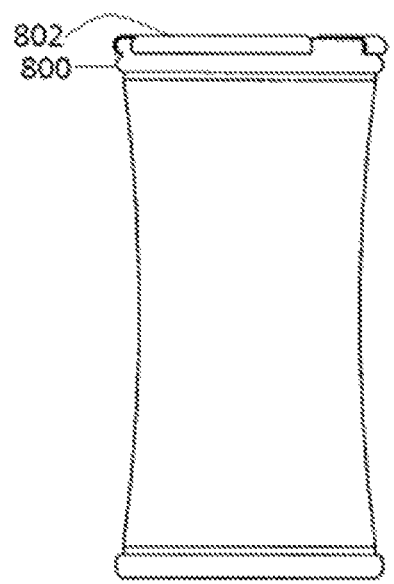
FIG. 3A illustrates a front view of a wound retractor having an outer ring system comprising a flexible outer ring with interchangeable rigid segments.
Figure 3B:
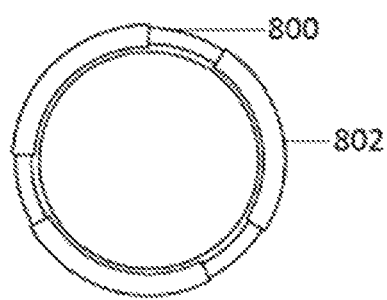
FIG. 3B illustrates a top view of the wound retractor of FIG. 3A.
Figure 3C:
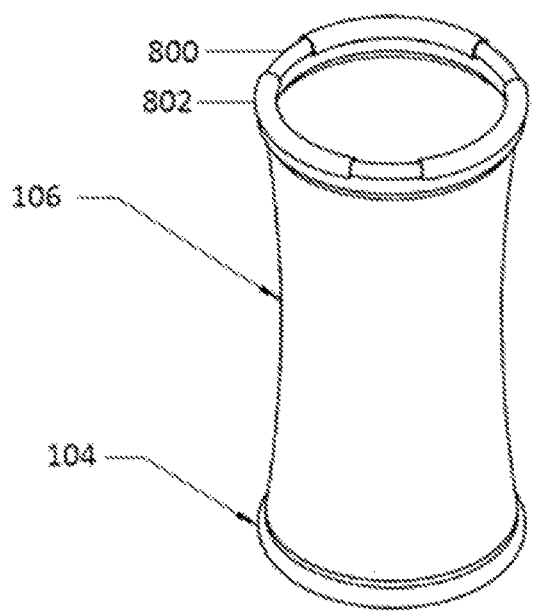
FIG. 3C illustrates a perspective view of the wound retractor of FIG. 3A.
Figure 4A:
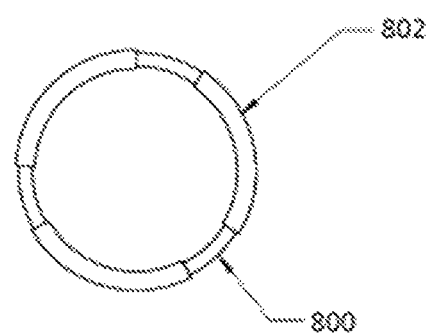
FIG. 4A illustrates a top view of the outer ring system of FIGS. 3A-C.
Figure 4B:
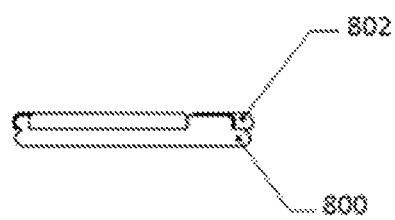
FIG. 4B illustrates a right view of the outer ring system of FIGS. 3A-C.

FIG. 3A shows a front view of the new wound retractor, in which three rigid segments 802 are snap fit onto the outer ring 800, better seen in top view FIG. 3B or auxiliary view FIG. 3C. The skilled artisan will appreciate that the number and dimensions of the rigid segments will vary depending on intended use. Thus, for example, rigid segments may have a shorter length, in which many more such segments can be attached to the outer ring, or a longer length, in which relatively few segments are attached to provide a more rigid outer ring. Varying the number and dimensions of the rigid segments will effectively modulate the rigidity of the outer ring. Similarly, the segments can be placed anywhere on the outer ring so as to provide different degrees of rigidity. While the rigid segments shown in FIG. 3 are substantially evenly placed around the outer ring, segments can be placed in regions of the outer ring where increased rigidity is desirable while leaving other portions of the outer ring more flexible, depending on the user's particular requirements. A close-up view of the rigid segments 802 attached to the outer ring 800 is shown in FIG. 4A (top view) and FIG. 4B (right view).

Figure 5A:
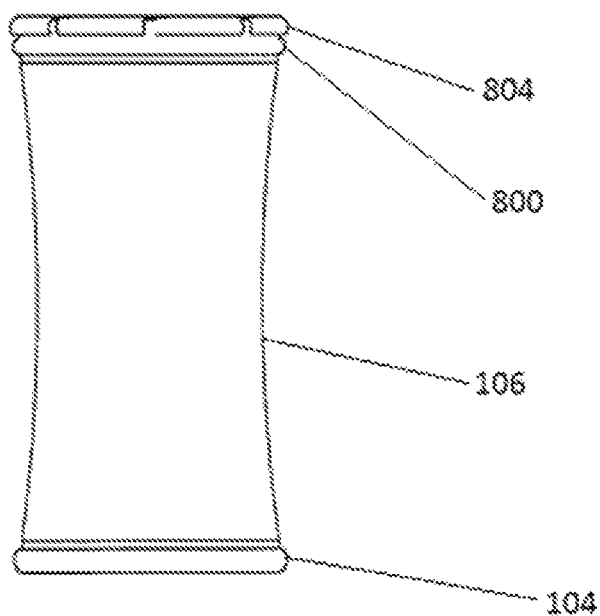
FIG. 5A illustrates an alternative embodiment of the wound retractor of FIGS. 3A-C, shown in front view.
Figure 5B:
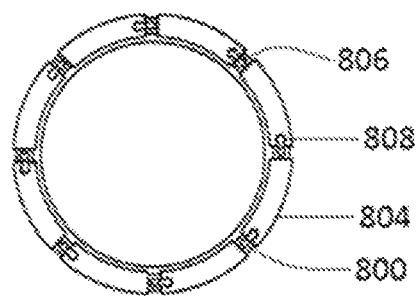
FIG. 5B illustrates a top view of the wound retractor of FIG. 5A.
Figure 5C:
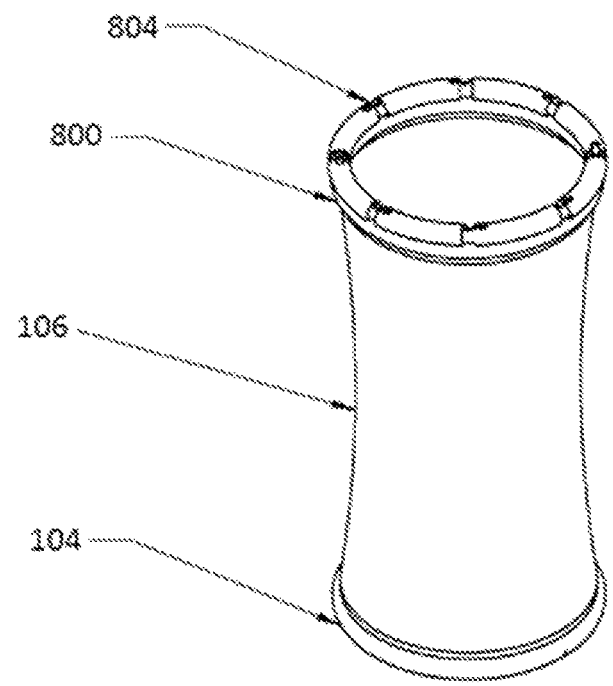
FIG. 5C illustrates a perspective view of the wound retractor of FIG. 5A.
Figure 6A:
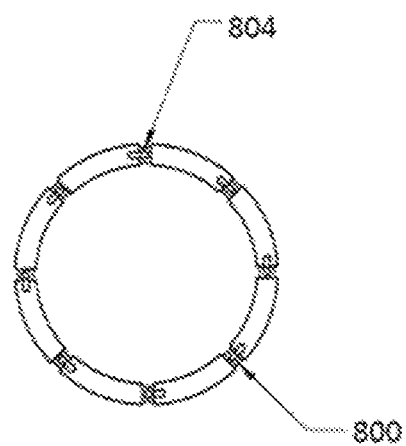
FIG. 6A illustrates the outer ring system of FIGS. 5A-C, shown in top view.
Figure 6B:
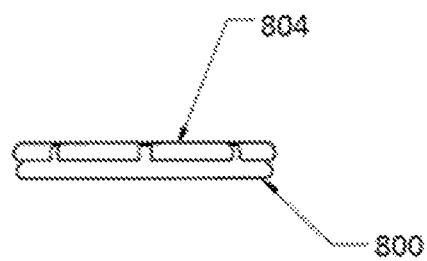
FIG. 6B illustrates the outer ring system of FIGS. 5A-C, shown in front view.

In the embodiment shown in FIGS. 3 and 4, the rigid segments are independent units, not linked together. In an alternative embodiment, as shown in FIGS. 5 and 6, interlockable rigid segments 804 comprise a boss 806 at one end and a recess 808 at the other, the recess adapted to receive the boss of an adjacent rigid segment to thereby link the segments together. In the illustrated embodiment, the interlinked rigid segments form a complete ring, which substantially covers the outer ring 800, best seen in FIG. 5B, 5C and FIG. 6B. It should be appreciated that the boss 806 can be rigid, for easier insertion into the recess 808, or relatively flexible, such that the shape of the interconnected ring of rigid segments 804 can conform to flexible outer rings of different shapes—e.g. circular, oval, elliptical and the like. Other interlocking devices besides a boss and recess are also contemplated in the present invention, including clamps, hooks and other interlocking means known in the art.

It should be appreciated that the outer ring system can be configured to have as many (or as few) rigid segments as needed. The rigid segments can be interconnected, as, for example, with a boss and recess configuration, or may attach to the outer ring independently. It should be further appreciated that providing rigidity to the outer ring with a series of discrete segments accommodates a range of sheath designs, such a circular, elliptical or other non-circular shapes.

Figure 7A:
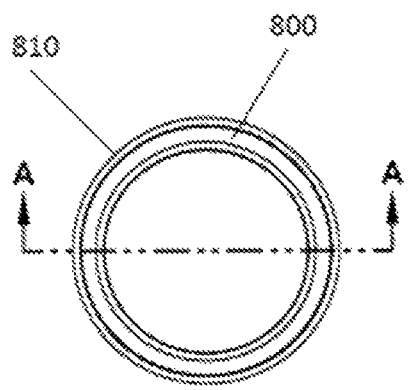
FIG. 7A illustrates a wound retractor having a flexible outer ring adapted to mount on a rigid base, shown in top view.
Figure 7B:
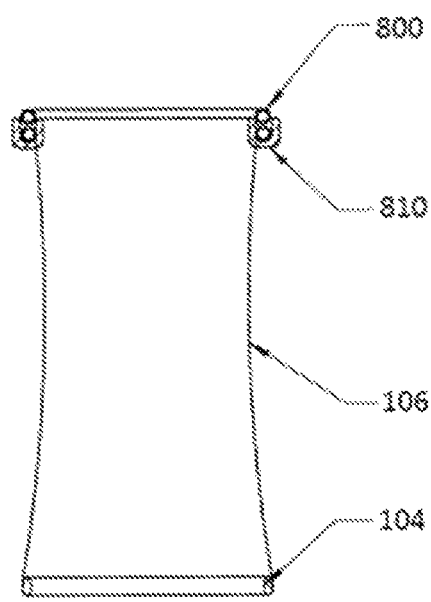
FIG. 7B illustrates a cross-sectional view of the wound retractor of FIG. 7A.
Figure 7C:
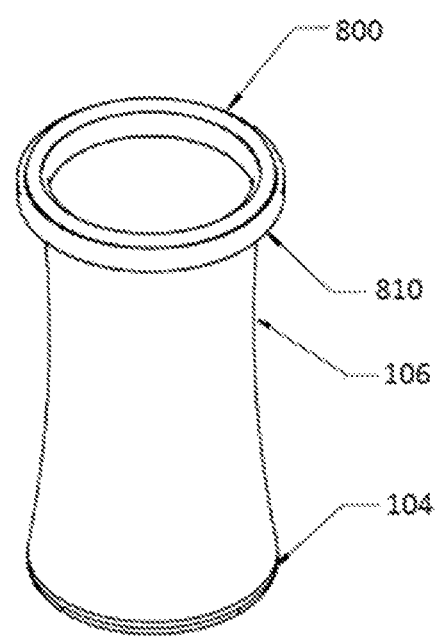
FIG. 7C illustrates a perspective view of the wound retractor of FIG. 7A.

In another embodiment, rigidity may be provided to a flexible outer ring by mounting the ring in a rigid base, allowing the wound to maintain its retracted shape during the duration of the procedure. For example, FIGS. 7 and 8 show a wound retractor in which a ring-shaped rigid base 810 is configured to receive the flexible ring 800 in an annular groove 812 disposed along the proximal or top surface of the base. In use, the retractor is deployed within the incision as described above and the wound retracted; the flexible outer ring 800 is then pulled up through the abdominal base and inserted into the annular groove 812.

Figure 9A:
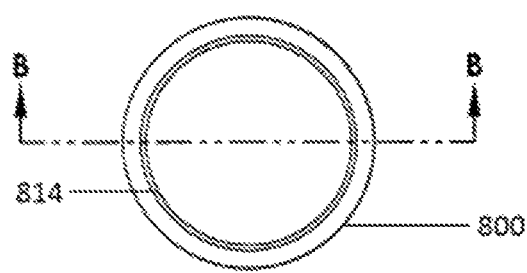
FIG. 9A illustrates a top view of an alternative embodiment of the wound retractor of FIGS. 7A-C.
Figure 9B:
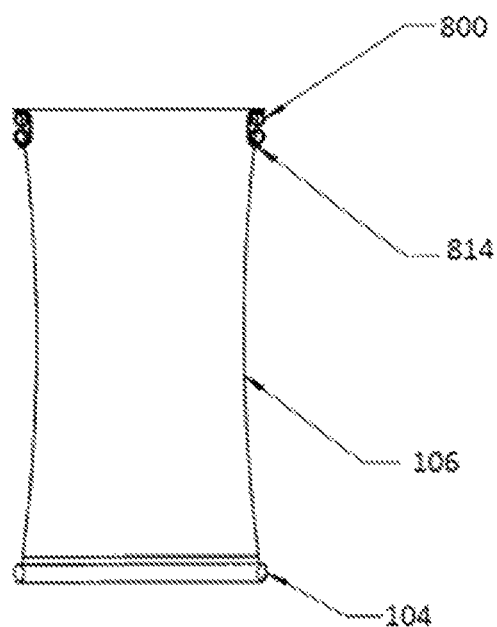
FIG. 9B illustrates a cross-sectional view of the wound retractor of FIG. 9A.
Figure 9C:
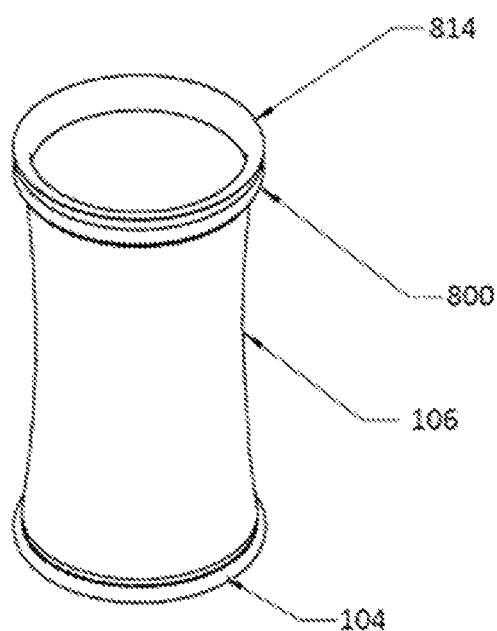
FIG. 9C illustrates a perspective view of the wound retractor of FIG. 9A.
Figure 10A:
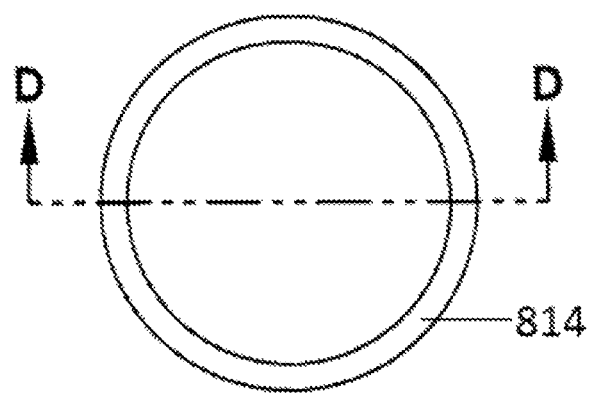
FIG. 10A illustrates the outer ring and rigid base of FIG. 9, shown in top view.
Figure 10B:
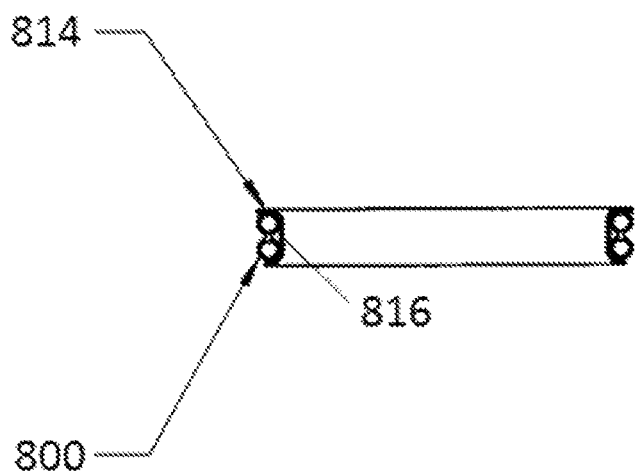
FIG. 10B illustrates the outer ring and rigid base of FIG. 9, shown in cross-sectional view.
Figure 10C:
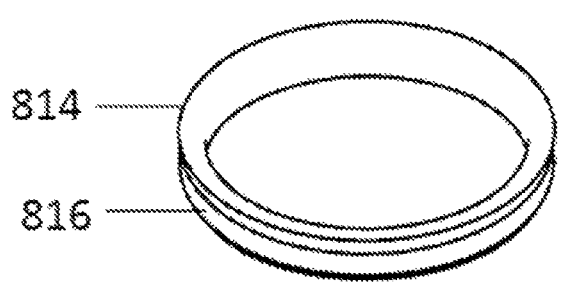
FIG. 10C illustrates the outer ring and rigid base of FIG. 9, shown in perspective view.

In an alternative embodiment, shown in FIGS. 9 and 10, the rigid base is configured to be deployed inside the flexible outer ring. In this embodiment, the ring-shaped rigid base 814 comprises an annular groove 816 along its outer circumference, adapted to receive the flexible ring 800. After the wound retractor is deployed into the round and the wound is retracted, the rigid base 814 is inserted inside the flexible outer ring 800, which is adapted to snap fit into the annular groove 816 to provide a rigid outer ring system.

The embodiments shown in FIGS. 7-10 are particularly suited to wound retractors adapted for use with a sealing cap. The rigid base, whether mounted under or inside the outer ring, may quickly and easily be added to the flexible outer ring to provide a uniform platform for attachment of a sealing cap. Gel caps suitable for use with wound retractors are described in detail in U.S. Pat. No. 8,267,858, the entire content of which is incorporated herein in its entirety.

Figure 11A:
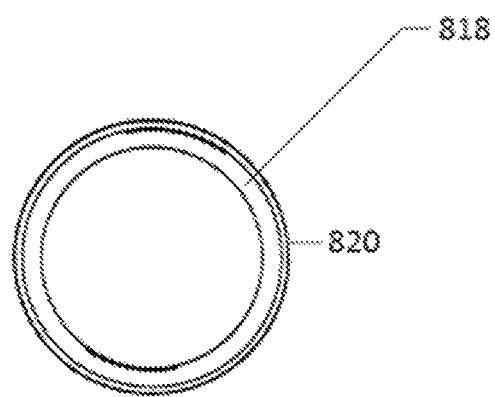
FIG. 11A illustrates a wound retractor having an imbedded magnetic strip, shown in top view.
Figure 11B:
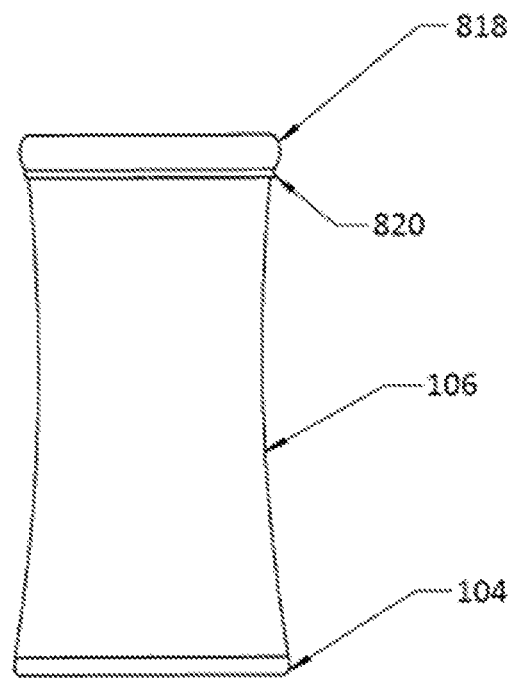
FIG. 11B illustrates a wound retractor having an imbedded magnetic strip, shown in front view.
Figure 11C:
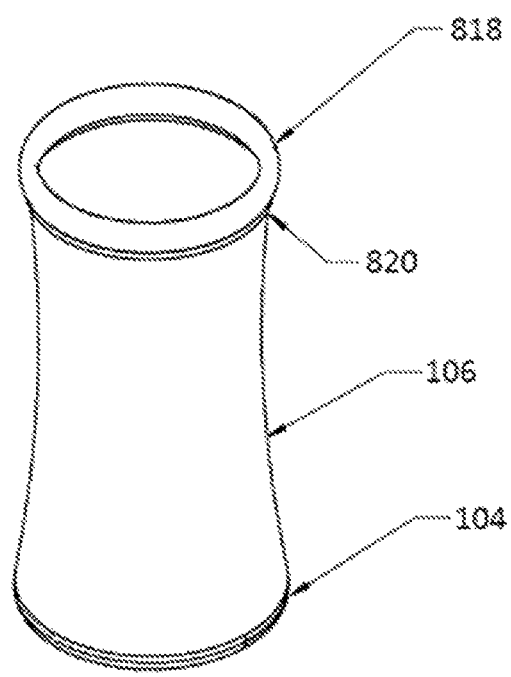
FIG. 11C illustrates a wound retractor having an imbedded magnetic strip, shown in perspective view.
Figure 12A:
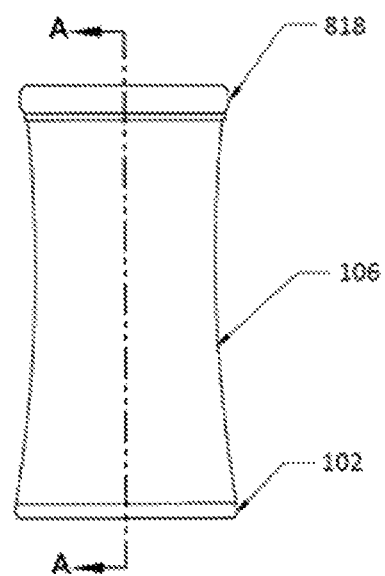
FIG. 12A illustrates a front view of the wound retractor of FIG. 11 with broken section lines.
Figure 12B:
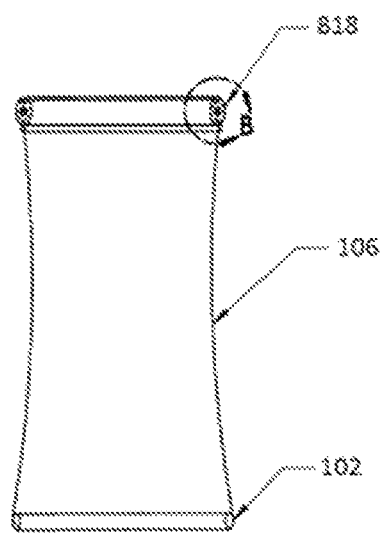
FIG. 12B illustrates a cross-sectional view of the wound retractor shown in FIG. 12A.
Figure 12C:
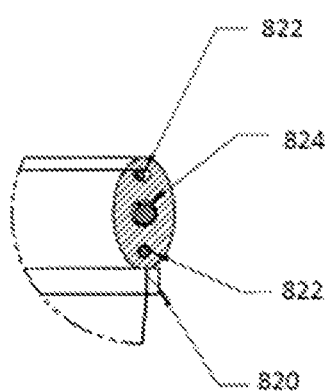
FIG. 12C illustrates a close-up view of the outer ring of the wound retractor of FIG. 11.

In still another embodiment, shown in FIGS. 11 and 12, the outer ring is detachable from the sheath. In this embodiment, the outer ring 818 attaches to the sheath 106 using magnetic attraction rather than conventional chemical or heat welding. A magnetic ring or strip 820 is imbedded in the proximal end of the sheath, while the outer ring comprises at least one magnetic or ferromagnetic ring 822 that attracts (or is attracted to) the magnetic strip 820. Optionally, a ferromagnetic strip may be imbedded in the proximal end of the sheath, while the outer ring comprises a magnetic ring. Optionally, as best shown in FIG. 12C, the outer ring may also comprise an elastic ring 823 and/or a rigid support ring 824.

Figure 13A:
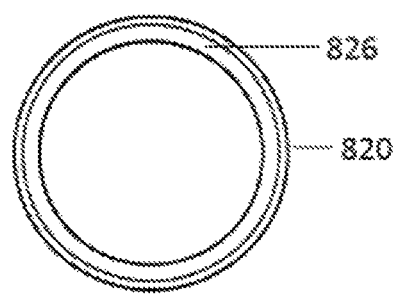
FIG. 13A illustrates an alternative embodiment of the wound retractor of FIG. 11, shown in top view.
Figure 13B:
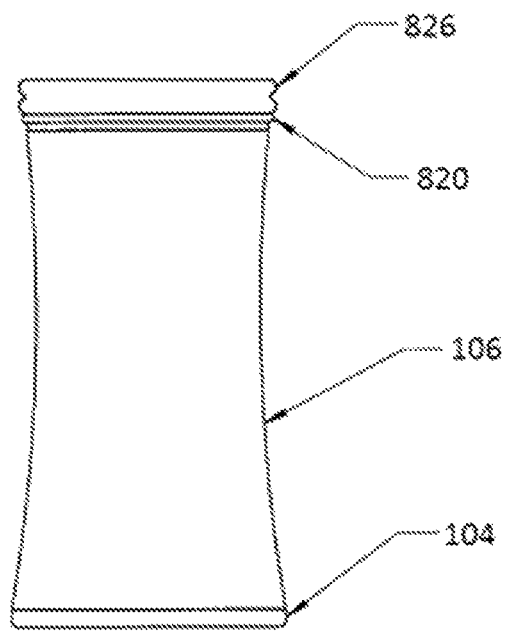
FIG. 13B illustrates an alternative embodiment of the wound retractor of FIG. 11, shown in front view.
Figure 13C:
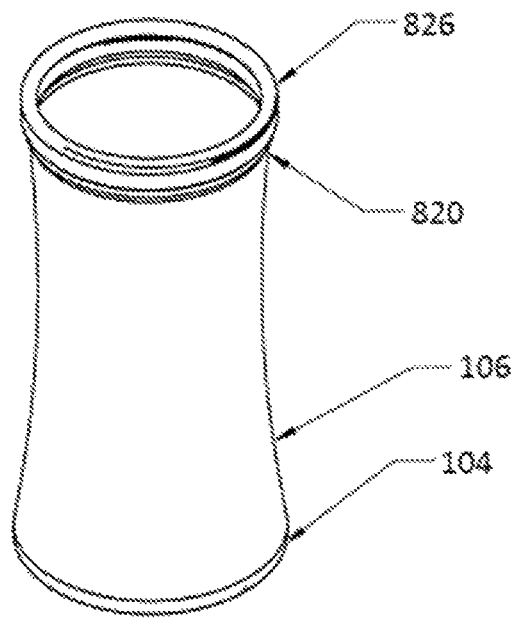
FIG. 13C illustrates an alternative embodiment of the wound retractor of FIG. 11, shown in perspective view.
Figure 14A:
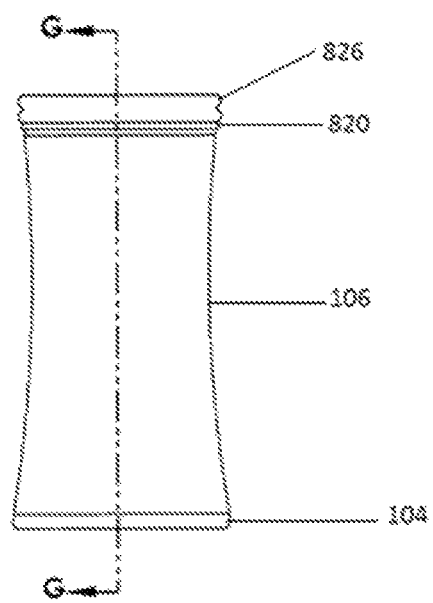
FIG. 14A illustrates a front view of the wound retractor of FIG. 13 with broken section lines.
Figure 14B:
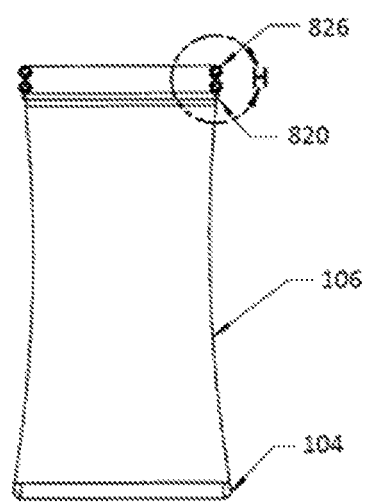
FIG. 14B illustrates a cross-sectional view of the wound retractor of FIG. 14A.
Figure 14C:
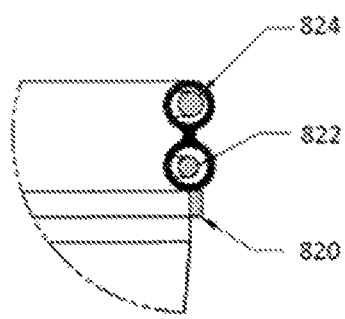
FIG. 14C illustrates a close-up view of the outer rings of the wound retractor of FIG. 13.

In yet another embodiment, the outer ring can be further configured to accept a sealing cap, such as a gel cap, to provide an instant seal of the body cavity while providing a working channel through the cap into the body cavity. In FIGS. 13 and 14, the wound retractor includes an outer ring 826 comprising two tubes, a first tube and a second tube, each having a lumen (see FIG. 14C). A rigid support ring 824 is disposed in the lumen of the first tube, providing a rigid base for attachment of a cap. A magnetic or ferromagnetic ring 822 is disposed in the lumen of the second tube, to attach the outer ring 826 to the magnetic ring 820 of the sheath 106. Optionally, a ferrous strip may be imbedded in the proximal end of the sheath, while a magnetic ring is disposed within the lumen of the second tube.

While certain embodiments have been particularly shown and described with reference to exemplary embodiments thereof, it will be understood by those of ordinary skill in the art that various changes in form and details may be made therein without departing from the spirit and scope thereof as defined by the following claims.

The invention claimed is:

1. A retractor/protector comprising:
   a flexible outer ring;
   an inner ring;
   a flexible sheath having a proximal end and a distal end and being disposed between the flexible outer ring and the inner ring; and
   a longitudinal axis defining an instrument access channel extending through the flexible sheath from the flexible outer ring to the inner ring,
   wherein the proximal end of the flexible sheath is de-attachably connected to the flexible outer ring via magnetic attraction and the distal end of the flexible sheath is attached to the inner ring,
   wherein the flexible outer ring comprises at least two separate tubes each having a respective lumen.

2. The retractor/protector of claim 1, wherein the flexible outer ring comprises a magnetic material configured to attract a corresponding magnetic material imbedded within the proximal end of the flexible sheath.

3. The retractor/protector of claim 1, wherein the flexible outer ring comprises a ferromagnetic material configured to attract a corresponding ferromagnetic material imbedded within the proximal end of the flexible sheath.

4. The retractor/protector of claim 1, wherein a first tube of the at least two separate tubes comprises a magnetic material or a ferromagnetic material configured to attract a corresponding magnetic material or ferromagnetic material imbedded within the proximal end of the flexible sheath.

5. The retractor/protector of claim 4, wherein a second tube of the at least two separate tubes comprises a rigid support ring.

6. The retractor/protector of claim 4, wherein a second tube of the at least two separate tubes comprises an elastic ring.

7. The retractor/protector of claim 1, wherein the flexible outer ring is configured to receive a sealing cap to provide a seal and a working channel through the sealing cap.

8. A retractor/protector comprising:
   a flexible outer ring;
   an inner ring;
   a flexible sheath having a proximal end and a distal end and being disposed between the flexible outer ring and the inner ring;
   a base having an inner circumference, an outer circumference, and a groove adapted to receive the flexible outer ring; and a longitudinal axis defining an instrument access channel extending through the flexible sheath from the flexible outer ring to the inner ring, wherein the proximal end of the flexible sheath is de-attachably connected to the flexible outer ring via magnetic attraction and the distal end of the flexible sheath is attached to the inner ring.

9. The retractor/protector of claim 8, wherein the base is configured to receive the flexible outer ring, wherein the flexible outer ring is configured to be pulled through the inner circumference of the base to be deployed into the groove disposed along a top surface of the base.

10. The retractor/protector of claim 8, wherein the groove is disposed along the outer circumference of the base and is configured to receive the flexible outer ring.

11. The retractor/protector of claim 8, wherein the flexible outer ring comprises a magnetic material configured to attract a corresponding magnetic material imbedded within the proximal end of the flexible sheath.

12. The retractor/protector of claim 8, wherein the flexible outer ring comprises a ferromagnetic material configured to attract a corresponding ferromagnetic material imbedded within the proximal end of the flexible sheath.

13. The retractor/protector of claim 8, wherein the flexible outer ring comprises at least two separate tubes each having a respective lumen.

14. The retractor/protector of claim 13, wherein a first tube of the at least two separate tubes comprises a magnetic material or a ferromagnetic material configured to attract a corresponding magnetic material or ferromagnetic material imbedded within the proximal end of the flexible sheath.

15. The retractor/protector of claim 14, wherein a second tube of the at least two separate tubes comprises a rigid support ring.

16. The retractor/protector of claim 14, wherein a second tube of the at least two separate tubes comprises an elastic ring.

17. The retractor/protector of claim 8, wherein the flexible outer ring is configured to receive a sealing cap to provide a seal and a working channel through the sealing cap.

\* \* \* \* \*